United States Patent
Manting et al.

(10) Patent No.: US 12,397,055 B2
(45) Date of Patent: Aug. 26, 2025

(54) METHODS OF TUMOR VACCINATION

(71) Applicant: MENDUS B.V., Leiden (NL)

(72) Inventors: Erik Hans Manting, Leiden (NL); Satwinder Kaur Singh, Leiden (NL); Jeroen Rovers, Leiden (NL)

(73) Assignee: MENDUS B.V., Leiden (NL)

( * ) Notice: Subject to any disclaimer, the term of this patent is extended or adjusted under 35 U.S.C. 154(b) by 585 days.

(21) Appl. No.: 17/580,919

(22) Filed: Jan. 21, 2022

(65) Prior Publication Data

US 2022/0249639 A1 Aug. 11, 2022

Related U.S. Application Data

(60) Provisional application No. 63/140,617, filed on Jan. 22, 2021.

(51) Int. Cl.
| | |
|---|---|
| A61K 40/42 | (2025.01) |
| A61K 39/00 | (2006.01) |
| A61K 40/19 | (2025.01) |
| A61K 40/24 | (2025.01) |
| A61P 35/00 | (2006.01) |

(52) U.S. Cl.
CPC .............. *A61K 40/42* (2025.01); *A61K 40/19* (2025.01); *A61K 40/24* (2025.01); *A61P 35/00* (2018.01); *A61K 2039/545* (2013.01); *A61K 2039/55* (2013.01); *A61K 2039/585* (2013.01); *A61K 2039/892* (2018.08)

(58) Field of Classification Search
CPC ............ A61K 39/4615; A61K 39/4644; A61K 39/4622; A61K 2039/892; A61K 2039/585; A61K 2039/552; A61K 2039/55; A61K 2039/545; A61K 2039/54; A61P 35/00

See application file for complete search history.

(56) References Cited

U.S. PATENT DOCUMENTS

| | | |
|---|---|---|
| 4,690,915 A | 9/1987 | Rosenberg |
| 4,797,368 A | 1/1989 | Carter et al. |
| 4,956,778 A | 9/1990 | Naito |
| 5,091,513 A | 2/1992 | Huston et al. |
| 5,132,405 A | 7/1992 | Huston et al. |
| 5,139,941 A | 8/1992 | Muzyczka et al. |
| 5,858,358 A | 1/1999 | June et al. |
| 5,876,989 A | 3/1999 | Berg et al. |
| 5,883,223 A | 3/1999 | Gray |
| 5,993,434 A | 11/1999 | Dev et al. |
| 5,994,136 A | 11/1999 | Naldini et al. |
| 6,013,516 A | 1/2000 | Verma et al. |
| 6,054,297 A | 4/2000 | Carter et al. |
| 6,080,840 A | 6/2000 | Slanetz et al. |
| 6,181,964 B1 | 1/2001 | Hofmann et al. |
| 6,207,156 B1 | 3/2001 | Kuchroo et al. |
| 6,233,482 B1 | 5/2001 | Hofmann et al. |
| 6,516,223 B2 | 2/2003 | Hofmann |
| 6,534,055 B1 | 3/2003 | June et al. |
| 6,567,694 B2 | 5/2003 | Hayakawa |
| 6,582,959 B2 | 6/2003 | Kim |
| 6,678,556 B1 | 1/2004 | Nolan et al. |
| 6,680,301 B2 | 1/2004 | Berg et al. |
| 6,692,964 B1 | 2/2004 | June et al. |
| 6,703,020 B1 | 3/2004 | Thorpe et al. |
| 6,797,514 B2 | 9/2004 | Berenson et al. |
| 6,867,041 B2 | 3/2005 | Berenson et al. |
| 6,884,879 B1 | 4/2005 | Baca et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,060,269 B1 | 6/2006 | Baca et al. |
| 7,067,318 B2 | 6/2006 | June et al. |
| 7,144,575 B2 | 12/2006 | June et al. |
| 7,171,264 B1 | 1/2007 | Hofmann et al. |
| 7,172,869 B2 | 2/2007 | June et al. |
| 7,173,116 B2 | 2/2007 | Fewell et al. |
| 7,175,843 B2 | 2/2007 | June et al. |
| 7,232,566 B2 | 6/2007 | June et al. |
| 7,569,664 B2 | 8/2009 | Jakobsen et al. |

(Continued)

FOREIGN PATENT DOCUMENTS

| | | |
|---|---|---|
| CA | 3104833 A1 | 1/2020 |
| EP | 0666868 B1 | 4/2002 |

(Continued)

OTHER PUBLICATIONS

Marabelle et al. Intratumoral immunotherapy: using the tumor as the remedy. Annals of Oncology (2017), 28(Suppl. 12), xii33-xii43. (Year: 2017).*
Cellosaurus entry to MVX-1 (first published 2022; retrieved from https://www.cellosaurus.org/CVCL_C3M8). (Year: 2022).*
Leaf et al. DCOne as an Allogeneic Cell-based Vaccine for Multiple Myeloma. J Immunother (2017), 40(9), 315-322. (Year: 2017).*
Santegoets et al. In vitro priming of tumor-specific cytotoxic T lymphocytes using allogeneic dendritic cells derived from the human MUTZ-3 cell line. Cancer Immunol Immunother (2006), 55, 1480-1490. (Year: 2006).*

(Continued)

*Primary Examiner* — Sean C. Barron
(74) *Attorney, Agent, or Firm* — LATHROP GPM LLP; James H. Velema, Esq.; Judith L. Stone-Hulslander, Esq.

(57) ABSTRACT

Provided herein are methods for treating a tumor or generating an immune response against a tumor in a subject in need, including one or more intratumoral administration steps each comprising administering to the subject at a tumor site, an effective amount of a first composition, and one or more vaccination steps each comprising administering to the subject at a site distal to the tumor site, an effective amount of a second composition. The first and second composition may each comprise an allogeneic leukemia-derived cell that is useful in eliciting an immune response against the tumor.

26 Claims, 6 Drawing Sheets

(56) References Cited

U.S. PATENT DOCUMENTS

| | | |
|---|---|---|
| 7,700,546 B2 | 4/2010 | Mekada et al. |
| 7,754,482 B2 | 7/2010 | Riley et al. |
| 8,008,449 B2 | 8/2011 | Korman et al. |
| 8,017,114 B2 | 9/2011 | Korman et al. |
| 8,066,989 B2 * | 11/2011 | Lindhofer .......... C07K 16/3053 |
| | | 424/93.1 |
| 8,119,129 B2 | 2/2012 | Jure-Kunkel et al. |
| 8,354,509 B2 | 1/2013 | Carven et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,507,443 B2 | 8/2013 | Mekada et al. |
| 8,586,363 B2 | 11/2013 | Voytas et al. |
| 8,697,853 B2 | 4/2014 | Voytas et al. |
| 8,722,400 B2 | 5/2014 | Riley et al. |
| 8,735,553 B1 | 5/2014 | Li et al. |
| 8,771,985 B2 | 7/2014 | Cui et al. |
| 9,187,758 B2 | 11/2015 | Cai et al. |
| 9,206,404 B2 | 12/2015 | Cui et al. |
| 9,393,257 B2 | 7/2016 | Osborn et al. |
| 9,555,105 B2 | 1/2017 | Riley et al. |
| 9,855,298 B2 | 1/2018 | Bot et al. |
| 9,861,689 B2 * | 1/2018 | Mach .................. A61K 9/0019 |
| 10,064,923 B2 | 9/2018 | Van Wetering et al. |
| 10,513,686 B2 | 12/2019 | Ostertag et al. |
| 11,027,001 B2 | 6/2021 | Van Wetering et al. |
| 11,052,144 B2 | 7/2021 | Van Wetering et al. |
| 11,071,778 B2 | 7/2021 | Van Wetering et al. |
| 12,091,681 B2 | 9/2024 | Manting et al. |
| 2003/0170238 A1 | 9/2003 | Gruenberg et al. |
| 2003/0190317 A1 | 10/2003 | Baca et al. |
| 2003/0203409 A1 | 10/2003 | Kim |
| 2003/0206899 A1 | 11/2003 | Ferrara et al. |
| 2004/0014645 A1 | 1/2004 | Draghia-Akli et al. |
| 2004/0057935 A1 * | 3/2004 | Yu .................... A61K 39/4611 |
| | | 424/93.7 |
| 2004/0059285 A1 | 3/2004 | Mathiesen et al. |
| 2004/0092907 A1 | 5/2004 | Mathiesen et al. |
| 2005/0052630 A1 | 3/2005 | Smith et al. |
| 2005/0070841 A1 | 3/2005 | Mathiesen et al. |
| 2005/0075308 A1 | 4/2005 | Wilson et al. |
| 2005/0112126 A1 | 5/2005 | Baca et al. |
| 2005/0186208 A1 | 8/2005 | Fyfe et al. |
| 2005/0196754 A1 | 9/2005 | Drmanac et al. |
| 2006/0009360 A1 | 1/2006 | Pifer et al. |
| 2006/0121005 A1 | 6/2006 | Berenson et al. |
| 2007/0041954 A1 | 2/2007 | Ichim |
| 2007/0128708 A1 | 6/2007 | Gamelin |
| 2012/0294796 A1 | 11/2012 | Johnson et al. |
| 2013/0274134 A1 | 10/2013 | Lindstedt et al. |
| 2013/0330399 A1 | 12/2013 | Reisfeld et al. |
| 2015/0166955 A1 | 6/2015 | Van Wetering et al. |
| 2015/0297698 A1 * | 10/2015 | Van Wetering .... A61K 40/4243 |
| | | 424/277.1 |
| 2018/0002397 A1 | 1/2018 | Shah et al. |
| 2018/0236054 A1 | 8/2018 | Sampson et al. |
| 2018/0346541 A1 | 12/2018 | Wong et al. |
| 2019/0000945 A1 | 1/2019 | Van Wetering et al. |
| 2019/0055297 A1 | 2/2019 | Zhao et al. |
| 2019/0134091 A1 | 5/2019 | Dropulic et al. |
| 2019/0151363 A1 | 5/2019 | Brentjens et al. |
| 2019/0263908 A1 | 8/2019 | Van Der Vliet et al. |
| 2020/0390876 A1 | 12/2020 | Manting et al. |
| 2020/0397883 A1 | 12/2020 | Manting et al. |
| 2021/0322471 A1 | 10/2021 | Manting et al. |
| 2021/0324332 A1 | 10/2021 | Manting et al. |
| 2021/0346479 A1 | 11/2021 | Van Wetering et al. |
| 2021/0401961 A1 | 12/2021 | Manting et al. |
| 2022/0023405 A1 | 1/2022 | Manting et al. |
| 2022/0023406 A1 | 1/2022 | Manting et al. |
| 2022/0168407 A1 | 6/2022 | Manting et al. |
| 2022/0249639 A1 | 8/2022 | Manting et al. |
| 2022/0305100 A1 | 9/2022 | Manting et al. |
| 2023/0355760 A1 | 11/2023 | Manting et al. |
| 2024/0002800 A1 | 1/2024 | Karlsson-Parra et al. |

FOREIGN PATENT DOCUMENTS

| | | |
|---|---|---|
| EP | 1894575 B1 | 2/2013 |
| EP | 2743344 A1 | 6/2014 |
| EP | 2931878 B1 | 11/2016 |
| WO | WO 1994/010202 A1 | 5/1994 |
| WO | WO 1996/007432 A1 | 3/1996 |
| WO | WO 1996/013593 A2 | 5/1996 |
| WO | WO 1996/018105 A1 | 6/1996 |
| WO | WO 1996/030046 A1 | 10/1996 |
| WO | WO 1996/040200 A1 | 12/1996 |
| WO | WO 1998/042752 A1 | 10/1998 |
| WO | WO 1998/045332 A2 | 10/1998 |
| WO | WO 1999/018129 A1 | 4/1999 |
| WO | WO 2000/037504 A2 | 6/2000 |
| WO | WO 2000/054708 A1 | 9/2000 |
| WO | WO 2000/054802 A2 | 9/2000 |
| WO | WO 2001/014424 A2 | 3/2001 |
| WO | WO 2001/018636 A1 | 3/2001 |
| WO | WO 2001/049317 A2 | 7/2001 |
| WO | WO 2001/093897 A2 | 12/2001 |
| WO | WO 2002/023994 A1 | 3/2002 |
| WO | WO 2002/044395 A1 | 6/2002 |
| WO | WO 2002/044396 A1 | 6/2002 |
| WO | WO 2003/020309 A2 | 3/2003 |
| WO | WO 2004/033685 A1 | 4/2004 |
| WO | WO 2005/012359 A2 | 2/2005 |
| WO | WO 2005/026318 A2 | 3/2005 |
| WO | WO 2005/040220 A1 | 5/2005 |
| WO | WO 2005/044853 A2 | 5/2005 |
| WO | WO 2006/000830 A2 | 1/2006 |
| WO | WO 2006/037960 A2 | 4/2006 |
| WO | WO 2006/121168 A1 | 11/2006 |
| WO | WO 2007/011693 A2 | 1/2007 |
| WO | WO 2008/119567 A2 | 10/2008 |
| WO | WO 2009/019320 A2 | 2/2009 |
| WO | WO 2009/034172 A1 | 3/2009 |
| WO | WO 2009/101611 A1 | 8/2009 |
| WO | WO 2009/114335 A2 | 9/2009 |
| WO | WO 2009/127988 A1 | 10/2009 |
| WO | WO 2010/037838 A2 | 4/2010 |
| WO | WO 2011/018636 A2 | 2/2011 |
| WO | WO 2011/044186 A1 | 4/2011 |
| WO | WO 2012/056236 A2 | 5/2012 |
| WO | WO 2012/136824 A1 | 10/2012 |
| WO | WO 2012/145493 A1 | 10/2012 |
| WO | WO 2013/025779 A1 | 2/2013 |
| WO | WO 2013/026833 A1 | 2/2013 |
| WO | WO 2013/026837 A1 | 2/2013 |
| WO | WO 2013/067492 A1 | 5/2013 |
| WO | WO 2013/181634 A2 | 12/2013 |
| WO | WO 2014/006058 A1 | 1/2014 |
| WO | WO 2014/087010 A1 | 6/2014 |
| WO | WO 2014/090795 A1 | 6/2014 |
| WO | WO 2014/138314 A1 | 9/2014 |
| WO | WO 2014/179664 A2 | 11/2014 |
| WO | WO 2014/194302 A2 | 12/2014 |
| WO | WO 2015/035606 A1 | 3/2015 |
| WO | WO 2015/073801 A1 | 5/2015 |
| WO | WO 2015/085847 A1 | 6/2015 |
| WO | WO 2015/112800 A1 | 7/2015 |
| WO | WO 2015/112900 A1 | 7/2015 |
| WO | WO 2016/149201 A2 | 9/2016 |
| WO | WO 2016/154628 A1 | 9/2016 |
| WO | WO 2016/176164 A1 | 11/2016 |
| WO | WO 2017/112797 A1 | 6/2017 |
| WO | WO 2017/134140 A1 | 8/2017 |
| WO | WO 2018/017020 A1 | 1/2018 |
| WO | WO 2018/075813 A1 | 4/2018 |
| WO | WO 2019/046815 A1 | 3/2019 |
| WO | WO 2019/075385 A1 | 4/2019 |
| WO | WO 2019/173636 A1 | 9/2019 |
| WO | WO 2019/177669 A1 | 9/2019 |
| WO | WO 2019/231846 A1 | 12/2019 |
| WO | WO 2020/014366 A1 | 1/2020 |
| WO | WO 2020/017962 A1 | 1/2020 |
| WO | WO 2020/019135 A1 | 1/2020 |
| WO | WO 2020/036977 A1 | 3/2020 |
| WO | WO 2020/043188 A1 | 10/2020 |

(56) References Cited

FOREIGN PATENT DOCUMENTS

| WO | WO 2020/208054 A1 | 10/2020 |
|---|---|---|
| WO | WO 2020/217226 A1 | 10/2020 |
| WO | WO 2021/216790 A1 | 10/2021 |

OTHER PUBLICATIONS

Van de Loosdrecht et al. A novel allogeneic off-the-shelf dendritic cell vaccine for postremission treatment of elderly patients with acute myeloid leukemia. Cancer Immunology, Immunotherapy (2018), 67, 1505-1518. (Year: 2018).*
Sarova et al. Characterization of Chromosome 11 Breakpoints and the Areas of Deletion and Amplification in Patients with Newly Diagnosed Acute Myeloid Leukemia. Genes, Chromosomes, & Cancer (2013), 52, 619-635. (Year: 2013).*
Aerts-Toegaert et al., "CD83 expression on dendritic cells and T cells: Correlation with effective immune responses", European Journal of Immunology, 37:686-695, 2007.
Agarwal et al., In Vivo Generation of CAR T Cells Selectively in Human CD4+ Lymphocytes Molecular Therapy 28(8):1783-1794 (2020).
Alemany, "Oncolytic Adenoviruses in Cancer Treatment", Biomedicines 2:36-49, 2014.
Alibakhshi et al., "Targeted cancer therapy through antibody fragments-decorated nanomedicines", J Control Release, 2017, 268: 323-334.
Alvey et al., "SIRPA-Inhibited, Marrow-Derived Macrophages Engorge, Accumulate, and Differentiate in Antibody-Targeted Regression of Solid Tumors", Current Biology, 27(14):2065-207, 2017.
Amir et al., "PRAME-Specific Allo-HLA-Restricted T Cells with Potent Antitumor Reactivity Useful for Therapeutic T-Cell Receptor Gene Transfer", Clinical Cancer Research, 17(17):5615-5625, 2011.
Andtbacka et al., "Talimogene Laherparepvec Improves Durable Response Rate in Patients With Advanced Melanoma", Journal of Clinical Oncology, 2015, 22(25): 2780-2788.
Anguille et al., "Dendritic cell vaccination as postremission treatment to prevent or delay relapse in acute myeloid leukemia", Blood, Oct. 2017, 130(15): 1713-1721.
Baars et al., "Skin tests predict survival after autologous tumor cell vaccination in metastatic melanoma: Experience in 81 patients", Annals of Oncology, 11(8):965-970, 2000.
Bell et al., "Crystal structure of nucleotide-free diphtheria toxin", Biochemistry, 1997, 36(3): 481-488.
Bengala, et al., Mobilization; Collection, and Characterization of Peripheral Blood Hemopoietic Progenitors after Chemotherapy with Epirubicin, Paclitaxel, and Granulocyte-Colony Stimulating Factor Administered to Patients with Metastatic Breast Carcinoma; Cancer; Mar. 1, 1998; vol. 82; No. 5; pp. 867-873.
Bergmann et al., "An endogenously synthesized decamer peptide efficiently primes cytotoxic T cells specific for the HIV-1 envelope glycoprotein", Eur J Immunol., 1993, 23(11): 2777-2781.
Bernhard et al., Generation of Immunostimulatory Dendritic Cells from Human CD34+ Hematopoietic Progenitor Cells of the Bone Marrow and Peripheral Blood, Cancer Research, 1995, pp. 1099-1104, vol. 55.
Bhaya et al., "CRISPR-Cas Systems in Bacteria and Archaea: Versatile Small RNAs for Adaptive Defense and Regulation", Annual Review Genetics, 45:273-297, 2011.
Bikard et al., "Programmable repression and activation of bacterial gene expression using an engineered CRISPR/Cas system", Nucleic Acids Research, 41(15):7429-7437, 2013.
Bommareddy et al., "Integrating oncolytic viruses in combination cancer immunotherapy", Nature Reviews Immunology, 2018, 18: 498-513.
Brocks et al., "A TNF receptor antagonistic scFv, which is not secreted in mammalian cells, is expressed as a soluble mono- and bivalent scFv derivative in insect cells", Immunotechnology 3(3):173-184 (1997).
Bürdek et al., "Three-day dendritic cells for vaccine development: Antigen uptake, processing and presentation", Journal of Translational Medicine, 8(90):1-13, 2010.
Buzzi et al., "Cancer immunity after treatment of Ehrlich tumor with diphtheria toxin", Cancer Res., Dec. 1974, 34(12): 3481-3486.
Buzzi et al., "CRM197: Effects of intravenous administration to advanced cancer patients", Cancer Res., Apr. 2004, 64(7 Supplement): 878.
Buzzi et al., "Diphtheria toxin in cancer therapy", The Lancet, 1974, 1(7858): 628-629.
Buzzi, "Diphtheria toxin treatment of human advanced cancer", Cancer Res., 1982, 42(5): 2054-2058.
Buzzi, et al., "CRM197 (nontoxic diphtheria toxin): effects on advanced cancer patients", Cancer Immunol. Immunother., 2004, 53: 1041-1048 (2004).
Buzzi, et al., "CRM197 and cancer: Effects of intratumoral administration", Therapy, Sep. 2004, 1(1): 61-66.
Buzzi, et al., "CRM197; Effects of intravenous administration to advanced cancer patients", American Association for Cancer Research, 2004, 64(7), Supplement.
Cermak et al., "Efficient design and assembly of custom TALEN and other TAL effector-based constructs for DNA targeting", Nucleic Acids Research, 39(12):e82-e82, 2011.
Chang et al., "A general method for facilitating heterodimeric pairing between two proteins: Application to expression of α and ß T-cell receptor extracellular segments", PNAS USA 91:11408-11412 (1994).
Chao et al., "Therapeutic Targeting of the Macrophage Immune Checkpoint CD47 in Myeloid Malignancies", Frontiers in Oncology, vol. 9, Art. 1380, pp. 1-9, 2019.
Cheever et al., "The Prioritization of Cancer Antigens: A National Cancer Institute Pilot Project for the Acceleration of Translational Research", Clinical Cancer Research, 15(17):5323-5337, 2009.
Chen et al., "Enhanced proofreading governs CRISPR-Cas9 targeting accuracy", Nature, 550(7676):407-410, 2017.
Chervin et al., "Engineering higher affinity T cell receptors using a T cell display system", The Journal of Immunology Methods 339(2):175-184 (2008).
Cho et al., "Targeted genome engineering in human cells with the Cas9 RNA-guided endonuclease", Nature Biotechnology, 31(3):230-232, 2013.
Chothia et al., "The outline structure of the T-cell αß receptor", The EMBO Journal 7(12):3745-3755 (1988).
Cignetti et al., CD34+ Acute Myeloid and Lymphoid Leukemic Blasts Can Be Induced to Differentiate Into Dendritic Cells, Blood, 1999, pp. 2048-2055, vol. 94.
Cohen et al., "Recognition of Fresh Human Tumor by Human Peripheral Blood Lymphocytes Transduced with a Bicistronic Retroviral Vector Encoding a Murine Anti-p53 TCR", The Journal of Immunology 175:5799-5808 (2005).
Cong et al., "Multiplex Genome Engineering using CRISPR/Cas Systems", Science, 339(6121):819-823, 2013.
Cougot et al., "'Cap-tabolism", Trends in Biochemical Science 29(8):436-444, (2004).
Cripe et al., "Phase 1 Study of Intratumoral Pexa-Vec (JX-594), an Oncolytic and Immunotherapeutic Vaccinia Virus, in Pediatric Cancer Patients", Molecular Therapy, 2015, 23(3): 602-608.
Danthinne et al., Production of first generation adenovirus vectors: a review, Gene Therapy, 7(20):1707-1714, 2000.
Davila et al., "CD19 CAR-Targeted T Cells Induce Long-Term Remission and B Cell Aplasia in an Immunocompetent Mouse Model of B Cell Acute Lymphoblastic Leukemia", PLOS ONE 8(4):e61338 (2013).
Davis et al., "Basic Methods in Molecular Biology," 1986.
Davodeau et al., "Secretion of Disulfide-linked Human T-cell Receptor γδ Heterdimers", The Journal of Biological Chemistry 268(21):15455-15460 (1993).
DCPRIME BV, "Leukemic Dendritic Cell Vaccination in Patients With Acute Myeloid Leukemia", ClinicalTrials.gov Identifier: NCT01373515, Retrieved from: <<https://clinicaltrials.gov/ct2/show/NCT01373515?term=NCT01373515&draw=2&rank=1>>, 5 pages, 2011.

(56) References Cited

OTHER PUBLICATIONS

De Gruijil et al., "Allogeneic dendritic cell (DC) vaccination as an "off the shelf" treatment to prevent or delay relapse in elderly acute myeloid leukemia patients: results of Phase I/IIa safety and feasibility study", Journal for Immunotherapy of Cancer, Supplement 1, No. P205, 2013.
Elango et al., "Optimized transfection of mRNA transcribed from a $d(A/T)_{100}$ tail-containing vector", Biochemical Biophysical Research Commun. 330:958-966 (2005).
EPO Comms, EP 08826916.2, dated Jan. 24, 2011, Jul. 20, 2012, and May 11, 2012.
Erben et al., "CS-1, A Novel c-kithi+ Acute Myeloid Leukemia Cell Line With Dendritic Cell Differentiation Capacity and Absent Immunogenicity", International Journal of Cancer, 105(2):232-240, 2003.
Ferlini et al.; A New Method to Evaluate in vitro Myelotoxicity of Antitumour Agents in the First Steps of Drug Development; Pharmacology & Toxicology 2001, 89; 231-236.
Ferrari et al.; Lack of dendritic cell mobilization into the peripheral blood of cancer patients following standard-or high-dose chemotherapy plus granulocyte-colony stimulating factor; Cancer Immunol Immunother; 2003; 52: 359-366.
Fife et al., "Inhibition of T cell activation and autoimmune diabetes using a B cell surface-linked CTLA-4 agonist", The Journal of Clinical Investigation 116(8):2252-2261 (2006).
Fiorentini et al., "Clinical experience of treatment of metastatic melanoma and solid tumours adopting a derivative of diphtheria toxin: cross-reacting material 197", In Vivo, 2013, 27(2): 197-202.
Frietze et al., "Engineering virus-like particles as vaccine platforms", Curr Opin Virol., 2016, 18: 44-49.
Gaj et al., "ZFN, TALEN, and CRISPR/Cas-based methods for genome engineering", Trends in Biotechnology, Jul. 2013, 31(7): 1-20, (Epub May 9, 2013).
Galluzzi et al., "Trial watch: Dendritic cell-based interventions for cancer therapy", OncoImmunology, 1(7):1111-1134, 2012.
Gao et al., "Selective elimination of leukemic CD34+ progenitor cells by cytotoxic T lymphocytes specific for WT1", Blood, 95(7):2198-2203, 2000.
Garboczi et al., "Assembly, Specific Binding, and Crystallization of a Human TCR-αβ with an Antigenic Tax Peptide from Human T Lymphotropic Virus Type 1 and the Class I MHC Moledule HLA-A2¹", The Journal of Immunology 157(12):5403-5410 (1996).
Garboczi et al., "Structure of the complex between human T-cell receptor, viral peptide and HLA-A2", Nature 384(6605):134-141 (1996).
Garfall et al., "T-cell phenotypes associated with effective CAR T-cell therapy in postinduction vs relapsed multiple myeloma", Blood Advances 3(19):2812-2815 (2019).
Geha et al., "The genetic basis of immunoglobulin-class switching", N Engl J Med., 1994, 330(14): 1008-1009.
Gilbert et al., "CRISPR-Mediated Modular RNA-Guided Regulation of Transcription in Eukaryotes", Cell, 154(2):442-451, 2013.
Gillis et al., "Contribution of human FcgRs to disease with evidence from human polymorphisms and transgenic animal studies", Frontiers in Immunology 5:254 (2014).
Giomarelli et al., "Inhibition of thrombin-induced platelet aggregation using human single-chain Fv antibodies specific for TREM-like transcript-1", Thromb Haemost 97(6):955-964 (2007).
Golden et al., "High-level production of a secreted, heterodimeric αβ murine T-cell receptor in Escherichia coli", Journal of Immunological Methods 206:163-169 (1997).
Graham et al., "A new technique for the assay of infectivity of human adenovirus 5 DNA", Virology, 1973, 52(2): 456-467.
Greiner et al., "High-dose RHAMM-R3 peptide vaccination for patients with acute myeloid leukemia, myelodysplastic syndrome and multiple myeloma", Haematologica, 95(7):1191-1197, 2010.
Greiner et al., "Identification and characterization of epitopes of the receptor for hyaluronic acid-mediated motility (RHAMM/CD168) recognized by CD8+ T Cells of HLA-A2-positive patients with acute myeloid leukemia", Blood, 106(3):938-945, 2005.

Grossardt et al., "Granulocyte-macrophage colony-stimulating factor-armed oncolytic measles virus is an effective therapeutic cancer vaccine", Human Gene Therapy, 2013, 24: 644-654.
Haddad, "Genetically Engineered Vaccinia Viruses As Agents for Cancer Treatment, Imaging, and Transgene Delivery", Frontiers in Immunology, 2017, 7: 96.
He et al., "CCL3 and CCL20-recruited dendritic cells modified by melanoma antigen gene-1 induce anti-tumor immunity against gastric cancer ex vivo and in vivo", Journal of Experimental & Clinical Cancer Research, 2010, 29: 37.
Hermans et al., "The VITAL assay: a versatile fluorometric technique for assessing CTL- and NKT-mediated cytotoxicity against multiple targets in vitro and in vivo", Journal of Immunological Methods 285(1):25-40 (2004).
Hermanson et al., "Utilizing chimeric antigen receptors to direct natural killer cell activity", Frontiers in Immunology 6(195):1-6 (2015).
Hirooka et al., "Comprehensive immunotherapy combined with intratumoral injection of zoledronate-pulsed dendritic cells, intravenous adoptive activated T lymphocyte and gemcitabine in unresectable locally advanced pancreatic carcinoma: a phase I/II trial", Oncotarget, 2018, 9(2): 2838-2847.
Ho et al., "Inhibition of cocaine binding to the human dopamine transporter by a single chain anti-idiotypic antibody: its cloning, expression, and functional properties", Biochima et Biophysica Acta 1638(3):257-266 (2003).
Holler et al., "In vitro evolution of a T cell receptor with high affinity for peptide/MHC", PNAS USA 97(10):5387-5392 (2000).
Holler et al., "TCRs with high affinity for foreign pMHC show self-reactivity", Nature Immunology 4(1):55-62 (2003).
Howells et al., "Oncolytic Viruses—Interaction of Virus and Tumor Cells in the Battle to Eliminate Cancer", Front Oncol., 2017, 7: 195.
Hu et al., "Evolved Cas9 variants with broad PAM compatibility and high DNA specificity", Nature, 556(7699):57-63, 2018.
Huang et al., "MIR-708 promotes phagocytosis to eradicate T-ALL cells by targeting CD47", Molecular Cancer, Jan. 24, 2018, 17(12): 1-6.
Huck et al., "Sequence of a human immunoglobulin gamma 3 heavy chain constant region gene: comparison with the other human Cy genes", Nucleic Acids Research 14(4):1779-1789 (1986).
Hudecek et al., "The Nonsignaling Extracellular Spacer Domain of Chimeric Antigen Receptors Is Decisive for In Vivo Antitumor Activity", Cancer Immunology Research 3(2):125-135 (2015).
Huston et al., "Protein engineering of antibody binding sites: Recovery of specific activity in an anti-digoxin single-chain Fv analogue produced in Escherichia coli", PNAS USA 85:5879-5883 (1988).
Hutzler et al., "Antigen-specific oncolytic MV-based tumor vaccines through presentation of selected tumor-associated antigens on infected cells or virus-like particles", Scientific Reports, 2017, 7: 16892.
Hwang et al., "Controlled differentiation of stem cells", Advanced Drug Delivery Reviews, 60(2):199-214, 2007.
International Search Report and Written Opinion for PCT International Application No. PCT/IB2020/053898, mailed Jul. 2, 2020.
International Search Report and Written Opinion for PCT International Application No. PCT/IB2021/052542, mailed Jun. 25, 2021.
International Search Report and Written Opinion for PCT International Application No. PCT/IB2021/055822, mailed Sep. 30, 2021.
International Search Report and Written Opinion for PCT International Application No. PCT/NL2019/050451, mailed Oct. 4, 2019.
International Search Report and Written Opinion for PCT International Patent Application No. PCT/EP2008/065391, mailed Feb. 26, 2009.
International Search Report and Written Opinion for PCT International Patent Application No. PCT/EP2013/076067, mailed Feb. 5, 2014.
International Search Report and Written Opinion for PCT International Patent Application No. PCT/IB2021/052543, mailed May 31, 2021.
International Search Report and Written Opinion for PCT International Patent Application No. PCT/IB2021/060233, mailed Apr. 4, 2022.

(56) References Cited

OTHER PUBLICATIONS

International Search Report and Written Opinion for PCT International Patent Application No. PCT/IB2022/052211 mailed Jul. 19, 2022.
Jinek et al., "RNA-programmed genome editing in human cells", eLife, 2:e00471, 2013.
Jores et al., "Resolution of hypervariable regions in T-cell receptor ß chains by a modified Wu-Kabat index of amino acid diversity", PNAS USA 87:9138-9142 (1990).
Jurincic-Winkler et al., "Antibody response to keyhole limpet hemocyanin (KLH) treatment in patients with superficial bladder carcinoma", Anticancer Res., 1996, 16(4A): 2105-2110.
Kleinstiver et al., "High-fidelity CRISPR-CAS9 variants with undetectable genome-wide off-targets," Nature, 529(7587):490-495, 2016.
Kloosterman et al., "Deciphering the pathogenic consequences of chromosomal aberrations in human genetic disease", Molecular Cytogenetics, 7(100):1-12, 2014.
Kochenderfer et al., "Construction and Pre-clinical Evaluation of an Anti-CD19 Chimeric Antigen Receptor", Journal of Immunotherapy 32(7):689-702 (2009).
Kohrt et al., "Donor immunization with WT1 peptide augments antileukemic activity after MHC-matched bone marrow transplantation", Blood, 118(19):5319-5329, 2011.
Kotb, "Bacterial Pyrogenic Exotoxins as Superantigens", Clinical Microbiology Reviews 8(3):411-426 (1995).
Koup et al., "Vaccine design for CD8 T lymphocyte responses", Cold Spring Harb Perspect Med., 2011, 1(1): a007252.
Krug et al., "WT1 Peptide Vaccinations Induce CD4 and CD8 T Cell Immune Responses in Patients With Mesothelioma and Non-small Cell Lung Cancer", Cancer Immunology, Immunotherapy, 59(10):1467-1479, 2010.
Kruisbeek, "Adoption of Cryostor® in Manufacturing of a Dendritic Cell Vaccine Platform", BioPreservation Today®, vol. 3, Issue 1, p. 10, 2011.
Kudo-Saito, et al., "Intratumoral vaccination and diversified subcutaneous/ intratumor vaccination with recombinant poxviruses encoding a tumor antigen and multiple costimulatory molecules", Clin Cancer Res., 2004, 10(3): 1090-1099.
Kurtzberg et al., "CD7+, CD4-, CD8-Acute Leukemia: A Syndrome of Malignant Pluripotent Lymphohematopoietic Cells", Blood, 73(2):381-390, 1989.
Lal et al., "Recombinant viruses with other anti-cancer therapeutics: a step towards advancement of oncolytic virotherapy", Cancer Gene Ther., 2018, 25: 216-226.
Larsson et al., "Functional and transcriptional profiling of MUTZ-3, a myeloid cell line acting as a model for dendritic cells", Immunology, 117:156-166, 2006.
Laurell et al., "Intratumorally injection pro-inflammatory allogeneic dendritic cells as immune enhancers: a first in-human study in unfavourable risk patients with metastatic renal cell carcinoma", Journal for Immunotherapy of Cancer 5:52 (2017).
Lawler et al., "Oncolytic Viruses in Cancer Treatment: A Review", JAMA Oncol. Review, 2017, 3(6): 841-849.
Lee et al., "ASTCT Consensus Grading for Cytokine Release Syndrome and Neurologic Toxicity Associated with Immune Effector Cells", Biology of Blood and Marrow Transplantation 25:625-638, doi.org/10.1016/j.bbmt.2018.12.758 (2019).
Lefranc et al., "IMGT unique numbering for immunoglobulin and T cell receptor variable domains and Ig superfamily V-like domains", Developmental and Comparative Immunology 27:55-77 (2003).
Li et al., "Directed evolution of human T-cell receptors with picomolar affinities by phage display", Nature Biotechnology 23(3):349-354 (2005).
Li et al., "Vaccination with CD47 deficient tumor cells elicits an antitumor immune response in mice", Nature Communications, 11:581, 2020.
Liu et al., "Pre-Clinical Development of a Humanized Anti-CD47 Antibody with Anti-Cancer Therapeutic Potential", PLoS One, 10(9): e0137345, 2015.
Logtenberg et al., "Glutaminyl cyclase in an enzymatic modifier of the CD47-SIRPα axis and target for cancer immunotherapy", Nat. Med., 25(4):612-619, 2019.
Lu et al., "Potential New Cancer Immunotherapy: Anti-CD47-SIRPα Antibodies", OncoTargets and Therapy, 13:9323-9331, 2020.
Lundstrom, K., "Viral Vectors in Gene Therapy", Diseases 6(2):42, DOI: 10.3390/diseases6020042 (2018).
Ma et al., "Preclinical development of a novel CD47 nanobody with less toxicity and enhanced anti-cancer therapeutic potential", Journal of Nanobiotechnology, 18:12, pp. 1-15, 2020.
Mali et al., "CAS9 transcriptional activators for target specificity screening and paired nickases for cooperative genome engineering", Nature Biotechnology, 31(9):833-838, 2013.
Mali et al., "RNA-Guided Human Genome Engineering via Cas9", Science, 339(6121):823-826, 2013.
Malito et al., "Structural basis for lack of toxicity of the diphtheria toxin mutant CRM197", Proc Natl Acad Sci U S A, 2012, 109(14): 5229-5234.
Marelli et al., "Oncolytic Viral Therapy and the Immune System: A Double-Edged Sword Against Cancer", Frontiers in Immunology, 2018, 9: 866.
Masterson et al., "MUTZ-3, a human cell line model for the cytokine-induced differentiation of dendritic cells from CD34+ precursors", Blood, 100(2):701-703, 2002.
May et al., "Peptide Epitopes From the Wilms' Tumor 1 Oncoprotein Stimulate CD4+ and CD8+ T Cells That Recognize and Kill Human Malignant Mesothelioma Tumor Cells", Clinical Cancer Research, 13(15):4547-4555, 2007.
Mishra et al., "Structural and immunological characterization of E. coli derived recombinant CRM197 protein used as carrier in conjugate vaccines", Bioscience reports, 2018, 38(5): BSR20180238.
Mitchell et al. "Tetanus toxoid and CCL3 improve dendritic cell vaccines in mice and glioblastoma patients", Nature 519(7543):366-369 (2015).
Miyamoto et al., "Heparin-binding epidermal growth factor-like growth factor as a novel targeting molecule for cancer therapy", Cancer Science 97(5):341-347 (2006).
Miyamoto, et al., "New approach to cancer therapy: heparin binding-epidermal growth factor-like growth factor as a novel targeting molecule", Anticancer Res., 2007, 27(6A): 3713-3721.
Mohan et al., "Applications of chemokines as adjuvants for vaccine immunotherapy", Immunobiology, 2018, 223(6-7): 477-485.
Moldenhauer et al., "Tumor Necrosis Factor Alpha-Stimulated Endothelium: An Inducer of Dendritic Cell Development from Hematopoietic Progenitors and Myeloid Leukemic Cells", Stem Cells, 22(2):144-157, 2004.
Moosmayer et al., "A single-chain TNF receptor antagonist is an effective inhibitor of TNF mediated cytotoxicity", Therapeutic Immunology, 2(10):31-40 (1995).
Morris, "Cryopreservation of Animal and Human Cell Lines", Methods in Molecular Biology, vol. 368: Cryopreservation and Freeze-Drying Protocols, 2nd Ed. (J. G. Day and G. N. Stacey eds.), Humana Press Inc. Totowa, N.J., pp. 227-236, .2007.
Moya et al., "Inhibition of Coated Pit Formation in $Hep_2$ Cells Blocks the Cytotoxicity of Diphtheria Toxin But Not That of Ricin Toxin", The Journal of Cell Biology 101(2):548-559 (1985).
Mumtaz et al., "Design of liposomes for circumventing the reticuloendothelial cells", Glycobiology 1(5):505-510 (1991).
Murata et al., "CD47-signal regulatory protein a signaling system and its application to cancer immunotherapy", Cancer Sci., Aug. 2018, 109(8): 2349-2357 (Epub Jul. 4, 2018).
Nacheva et al., "Preventing nondesired RNA-primed RNA extension catalyzed by T7 RNA polymerase", Eur. J. Biochem. 270:1485-1465 (2003).
Nagasawa et al., "DCP-001 stimulates T cell proliferation and increases memory CD4 + T cells in OC patients' PBMC Preclinical studies support therapeutic application of the leukemic cell-based cancer relapse vaccine DCP-001 in ovarian cancer", Nov. 1, 2020, Retrieved from the Internet: URL:https://immunicum.se/wp-content/uploads/2021/04/Poster-DCprime_SITC2020-FINAL.pdf.
Nam, et al., "Anti-tumor Effect of Intravenous Administration of CRM197 for Triple-negative Breast Cancer Therapy", Anticancer Res., 2016, 36(7): 3651-3657.

(56) References Cited

OTHER PUBLICATIONS

Narita et al., "WT1 Peptide Vaccination in Combination With Imatinib Therapy for a Patient With CML in the Chronic Phase", International Journal of Medical Sciences, 7(2):72-81, 2010.
Neelapu et al., "Chimeric antigen receptor T-cell therapy—assessment and management of toxicities", Nat Rev Clin Oncology 15(1):47-62 (2018).
Neuhaus et al., Multiple sclerosis: Mitoxantrone promotes differential effects on immunocompetent cells in vitro; Journal of Neuroimmunology 168: 128-137 (2005).
Nguyen-Hoai et al., "CCL21 (SLC) improves tumor protection by a DNA vaccine in a Her2/neu mouse tumor model", Cancer Gene Therapy, 2012, 19: 69-76.
Nijman et al., "Phase 1 Study to Evaluate the Safety, Feasibility and Immunogenicity of an Allogeneic, Cell-based Vaccine (DCP-001) in High Grade Serous Ovarian Cancer Patients After Primary Treatment (ALISON)", Feb. 4, 2021, Retrieved from the Internet: URL:https://clinicaltrials.gov/ct2/show/NCT04739527.
Ochsenreither et al., "Wilms Tumor Protein 1 (WT1) Peptide Vaccination—induced Complete Remission in a Patient With Acute Myeloid Leukemia is Accompanied by the Emergence of a Predominant T-cell Clone Both in Blood and Bone Marrow", Journal of Immunotherapy, 34(1):85-91, 2011.
Olusanya et al., "Liposomal Drug Delivery Systems and Anticancer Drugs", Molecules, 2018, 23(4): 907.
Palucka et al., "Recent Developments in Cancer Vaccines", The Journal of Immunology, 186(3):1325-1331, 2011.
Park et al., "Are All Chimeric Antigen Receptors Created Equal?", Journal of Clinical Oncology 33(6):651-653 (2015).
Parkhurst et al., "Characterization of Genetically Modified T-Cell Receptors that Recognize the CEA:691-699 Peptide in the Context of HLA-A2.1 on Human Colorectal Cancer Cells", Clinical Cancer Research 15(1):169-180 (2009).
Peter et al., "Protective effects of an anti-melanocortin-4 receptor scFv derivative in lipopolysaccharide-induced cachexia in rats", J Cachexia Sarcopenia Muscle Aug. 12, 2012.
Peter et al., "scFv Single Chain Antibody Variable Fragment as Inverse Agonist of the ß$_2$-Adrenergic Receptor", The Journal of Biological Chemistry 278(38):36740-36747 (2003).
Qi et al., "Repurposing CRISPR as an RNA-Guided Platform for Sequence-Specific Control of Gene Expression", Cell, 152(5): 1173-1183, 2013.
Quintarelli et al., "Cytotoxic T lymphocytes directed to the preferentially expressed antigen of melanoma (PRAME) target chronic myeloid leukemia", Blood, 112(5):1876-1885, 2008.
Quintarelli et al., "High-avidity cytotoxic T lymphocytes specific for a new PRAME-derived peptide can target leukemic and leukemic-precursor cells", Blood, 117(12):3353-3362, 2011.
Rezvani et al., "Leukemia-associated antigen-specific T-cell responses following combined PR1 and WT1 peptide vaccination in patients with myeloid malignancies", Blood, 111(1):236-242, 2008.
Rezvani et al., "T-Cell Responses Directed against Multiple HLA-A* 0201-Restricted Epitopes Derived from Wilms' Tumor 1 Protein in Patients with Leukemia and Healthy Donors: Identification, Quantification, and Characterization", Clinical Cancer Research, 11(24):8799-8807, 2005.
Rosato et al., "Virus-specific memory T cells populate tumors and can be repurposed for tumor immunotherapy", Nature Communications 10:567 (2019).
Rosenberg "Cell transfer immunotherapy for metastatic solid cancer-what clinicians need to know", Nat Rev Clinical Oncology 8(10):577-585 (2011).
Rosenfeld et al., "WT1 in acute leukemia, chronic myelogenous leukemia and myelodysplastic syndrome: therapeutic potential of WT1 targeted therapies", Leukemia, 17:1301-1312, 2003.
Santegoets et al., "A CD34+ Human cell line model of myeloid dendritic cell differentiation: evidence for a CD14+CD11b+ Langerhans cell precursor", Journal of Leukocyte Biology, 80:1337-1344, 2006.

Santegoets et al., "In vitro priming of tumor-specific cytotoxic T lymphocytes using allogeneic dendritic cells derived from the human MUTZ-3 cell line", Cancer Immunology, Immunotherapy, 55:1480-1490, 2006.
Saxena et al., "Re-emergence of Dendritic Cell Vaccines for Cancer Treatment", Trends in Cancer, 2018, 4:2: 119-137.
Schenborn et al., "A novel transcription property of SP6 and T7 RNA polymerases: dependence on template structure", Nucleic Acids Research 13:6223-36 (1985).
Scheraga "Predicting Three-Dimensional Structures of Oligopeptides" Reviews in Computational Chemistry 2:73-142 (1992).
Schlueter et al., "Specificity and Binding Properties of a Single-chain T Cell Receptor", J. Mol. Biol. 256:859-869 (1996).
Schmitt et al., "Chronic myeloid leukemia cells express tumor-associated antigens eliciting specific CD8+ T-cell responses and are lacking costimulatory molecules", Experimental Hematology, 34(12):1709-1719, 2006.
Schmitt et al., "RHAMM-R3 peptide vaccination in patients with acute myeloid leukemia, myelodysplastic syndrome, and multiple myeloma elicits immunologic and clinical responses", The Journal of the American Society of Hematology, 111(3):1357-1365, 2008.
Shankar et al., "Interferon-[gamma] Added During Bacillus Calmette-Guerin Induced Dendritic Cell Maturation Stimulates Potent T h 1 Immune Responses", Oct. 10, 2003, Retrieved from the Internet: URL:https://link.springer.com/content/pdf/10.1186/1479-5876-1-7.pdf.
Shen et al. "Engineering Peptide Linkers for scFv Immunosensors", Anal. Chem. 80(6):1910-1917 (2008).
Shieh et al., "Transgenic Expression of Single-Chain Anti-CTLA-4 Fv on ß Cells Protects Nonobese Diabetic Mice from Autoimmune Diabetes", The Journal of Immunology 183(4):2277-2285 (2009).
Slaymaker et al., "Rationally engineered Cas9 nucleases with improved specificity", Science, 351(6268): 84-88, 2016.
Smith, et al., "In situ programming of leukaemia-specific T cells using synthetic DNA nanocarriers", Nat. Nanotechnology 12(8):813-820 (2017).
Sockolosky et al., "Durable antitumor responses to CD47 blockade require asaptive immune stimulation", PNAS, 113(19):E2646-2654, 2016.
Sommandas et al., "Novel vaccination strategies using tumour-independent antigens to induce anti-tumour immunity in solid tumours", Journal for Immunotherapy of Cancer 7(Suppl. 1):P687 (2019) & 34$^{th}$ Annual Meeting of the Society for Immunotherapy of Cancer, National Harbour, MD, USA, Nov. 10, 2019.
Sommermeyer et al., "Chimeric antigen receptor-modified T cells derived from defined CD8+ and CD4+ subsets confer superior antitumor reactivity in vivo", Leukemia 30(2):492-500 (2016).
Stepinski et al., "Synthesis and properties of mRNAs containing the novel "anti-reverse" cap analogs 7-methyl(3'-O-methyl)GpppG and 7-methyl(3'-deoxy)GpppG", RNA, 7:1468-1495 (2001).
Stickings, et al., "Transcutaneous immunization with cross-reacting material CRM(197) of diphtheria toxin boosts functional antibody levels in mice primed parenterally with adsorbed diphtheria toxoid vaccine", Infect Immun., 2008, 76(4):1766-1773.
Subhadra et al., "Inducing Tumor Suppressive Microenvironments through Genome Edited CD47-/- Syngeneic Cell Vaccination", Scientific Reports, Dec. 27, 2019, 9(1): 20057.
Suhrbier, "Multi-epitope DNA vaccines", Immunol Cell Biol., 1997, 75(4): 402-408.
Tack et al., "Phenotypic and genomic analysis of an exceptional case of enteropathy associated T-cell lymphoma", Leukemia Research, 34(8):e183-e189, 2010.
Tacken et al., "Effective induction of naive and recall T-cell responses by targeting antigen to human dendritic cells via a humanized anti-DC-SIGN antibody", Blood, 2005, 106(4): 1278-1285.
Tan et al., "Influence of the hinge region on complement activation, C1q binding, and segmental flexibility in chimeric human immunoglobulins", PNAS USA 87(1): 162-166 (1990).
Teachey et al. "Identification of Predictive Biomarkers for Cytokine Release Syndrome afer Chimeric Antigen Receptor T-cell Therapy for Acute Lymphoblastic Leukemia", Cancer Discovery 6(6):664-679 (2016).

(56) References Cited

OTHER PUBLICATIONS

Themeli et al., "Generation of tumor-targeted human T lymphocytes from induced pluripotent stem cells for cancer therapy", Nature Biotechnology 31(10):928-933 (2013).
Thurner et al., "Generation of large numbers of fully mature and stable dendritic cells from leukapheresis products for clinical application", Journal of Immunological Methods, 223(1):1-15, 1999.
Töpfer et al., "DAP12-Based Activating Chimeric Antigen Receptor for NK Cell Tumor Immunotherapy", The Journal of Immunology 194(7):3201-3212 (2015).
Triozzi et al., "Intratumoral injection of dendritic cells derived in vitro in patients with metastatic cancer", Cancer, 2000, 89(12): 2646-2654.
Tseng et al., "Anti-CD47 antibody-mediated phagocytosis of cancer by macrophages primes an effective antitumor T-call response", PNAS, 110(27):11103-11108, 2013.
Tsukahara et al., "CD19 target-engineered T-cells accumulate at tumor lesions in human B-cell lymphoma xenograft mouse models", Biochem Biophys Res Commun 438(1):84-89 (2013).
Twumasi-Boateng et al., "Oncolytic viruses as engineering platforms for combination immunotherapy", Nature Reviews Cancer 18:419-432 (2018).
Uchida et al., "Mutation in the structural gene for diphtheria toxin carried by temperate phage", Nat New Biol., 1971, 233(35): 8-11.
Ud Din et al., "Effective use of nanocarriers as drug delivery systems for the treatment of selected tumors", Int J Nanomedicine, 2017, 12: 7291-7309.
Ueno et al., "Harnessing Human Dendritic Cell Subsets for Medicine", Immunological Reviews, 234(1):199-212, 2010.
Van De Ven et al., "Exposure of CD34+ precursors to cytostatic anthraquinone-derivatives induces rapid dendritic cell differentiation: implications for cancer immunotherapy", Cancer Immunology, Immunotherapy, Springer, Berlin, DE, 61(2):181-191, 2011.
Van Helden et al., "Human and murine model cell lines for dendritic cell biology evaluated", Immunology Letters, 117(2):191-197, 2008.
Van Nuffel et al., "Loading of dendritic cells for immunotherapy", ISBT Science Series, 2013, 8: 161-164.
Van Tendeloo et al., "Induction of complete and molecular remissions in acute myeloid leukemia by Wilms' tumor 1 antigen-targeted dendritic cell vaccination", PNAS, 107(31):13824-13829, 2010.
Varela-Rohena et al., "Control of HIV-1 immune escape by CD8 T-calls expressing enhanced T-cell receptor", Nat Med. 14(12):1390-1395 (2008).
Vermeij et al., "Potential Target Antigens for a Universal Vaccine in Epithelial Ovarian Cancer", Clinical and Developmental Immunology, vol. 2010, Article ID 891505, pp. 1-8. 2010.
Vigneron et al., "Database of T cell-defined human tumor antigens: the 2013 update", Cancer Immunity, 2013, 13: 15.
Wadelin et al., "Leucine-rich repeat protein PRAME: expression, potential functions and clinical implications for leukemia", Molecular Cancer, 9(1):1-10, 2010.
Wallgren et al., "Direct Allorecognition Promotes Activation of Bystander Dendritic Cells and Licenses Them for Th1 Priming: A Functional Link Between Direct and Indirect Allosensitization", Scandinavian Journal of Immunology 62:234-242 (2005).
Wang et al., "CMVpp65 Vaccine Enhances the Antitumor Efficacy of Adoptively Transferred CD19-Redirected CMV-Specific T Cells", Clinical Cancer Research 21(13):2993-3002 (2015).
Weiskopf et al., "CD47-blocking immunotherapies stimulate macrophage-mediated destruction of small-cell lung cancer", Journal of Clinical Investigation, 126(7):2610-2620, 2016.
Weiskopf et al., "Engineered SIRPα Variants as Immunotherapeutic Adjuvants to Anticancer Antibodies", Science, 341(6141):88-91, 2013.
Welte et al., "Purification and biochemical characterization of human pluripotent hematopoietic colony-stimulating factor", PNAS, 82(5):1526-1530, 1985.
Westers et al., Rapid generation of antigen-presenting cells from leukaemic blasts in acute myeloid leukaemia, Cancer Immunology, Immunotherapy. 2003, pp. 17-27, vol. 52.
Wlodarska et al., "A New Subtype of Pre-B Acute Lymphoblastic Leukemia With t(5;12)(q31q33;p12), Molecularly and Cytogenetically Distinct From t(5;12) in Chronic Myelomonocytic Leukemia", Blood, 89(5):1716-1722, 1997.
Xie et al., "Direct demonstration of MuSK involvement in acetylcholine receptor clustering through identification of agonist ScFv", Nature Biotechnology 15(8):768-771 (1997).
Yan et al., "Engineering Upper Hinge Improves Stability and Effector Function of a Human lgG1", The Journal of Biological Chemistry 287(8):5891-5897 (2012).
Yilmaz et al., Activated myeloid dendritic cells accumulate and colocalize with CD3+ T cells in coronary artery lesions in patients with Kawasaki disease, Experimental Molecular Pathology 2007, pp. 93-103, vol. 83, No. 1.
Zhang et al., "Advances in Anti-Tumor Treatments Targeting the CD47/SIRPα Axis", Frontiers Immunology, vol. 11, Art. 18, pp. 1-15, 2020.
Zhang et al., "An NKp30-Based Chimeric Antigen Re3ceptor Promotes T Cell Effector Functions and Antitumor Efficacy In Vivo", The Journal of Immunology 189(5):2290-2299 (2012).
Zhao et al., "Characteristics of an scFv Antibody Fragment That Binds to Immunoglobulin G of Graves' Disease Patients and Inhibits Autoantibody-Mediated Thyroid-Stimulating Activity", Hybridoma 27(6):455-451 (2008).
Zhao et al., "Multiple injections of electroporated autologous T cells expressing a chimeric antigen receptor mediate regression of human disseminated tumor", Cancer Research 70(22):9053-9061 (2010).
Zhou et al., "Exclusive Transduction of Human CD4+ T Cells upon Systemic Delivery of CD4-Targeted Lentiviral Vectors", The Journal of Immunology 195(5):2493-2501 (2015).
Zhou et al., "T-cell receptor gene transfer exclusively to human CD8+ cells enhances tumor cell killing", Blood 120(22):4334-4342 (2012).
Zibera, et al.; An epirubicin/paclitaxel combination mobilizes large amounts of hematopoietic progenitor cells in patients with metastatic breast cancer showing optimal response to the same chemotherapy regimen; Haematologica 1999; 84:924-929.
Zuo et al., "Transfer of Cellular Content from the Allogeneic Cell-Based Cancer Vaccine DCP-001 to Host Dendritic Cells Hinges on Phosphatidylserine and Is Enhanced by CD47 Blockade", Cells, Nov. 19, 2021, 10(11): 3233.
Akahori et al., "Antitumor of CAR-T cells targeting the intracellular onco-protein WT1 can be enhanced by vaccination", Blood, 2018, 132(11): 1134-1145.
Bamias et al., "Four Cycles of paclitaxel and carboplatin as adjuvant treatment in early-stage ovarian cancer: a six-year experience of the Hellenic Cooperative Oncology Group", BMC Cancer, Sep. 25, 2006, 6(228): 1-8.
Batich et al., "Long-term Survival in Glioblastoma with Cytomegalovirus pp65- Targeted Vaccination", Clin Cancer Res., Apr. 15, 2017, 23(8): 1898-1909.
Da Costa Miranda et al., "Neoadjuvant chemotherapy with six cycles of carboplatin and paclitaxel in advanced ovarian cancer patients unsuitable for primary surgery: Safety and effectiveness", Gynecol. Oncol., Feb. 2014, 132(2): 287-291.
Dao et al., "An immunogenic WT1-derived peptide that induces T cell response in the context of HLA-A*02:01 and HLA-A*24:02 molecules", Oncoimmunology, 2017, 6(2): e1252895, published online Dec. 7, 2016.
Dranoff et al., "Vaccination with irradiated tumor cells engineered to secrete murine granulocyte-macrophage colony-stimulating factor stimulates potent, specific, and long-lasting anti-tumor immunity", PNAS USA, Apr. 1993, 90: 3539-3543.
Granzin et al., "Shaping of Natural Killer Cell Antitumor Activity by Ex Vivo Cultivation", Frontiers in Immunology, Apr. 26, 2017, 8: 18 pages.
Guo et al., "The plasticity and potential of leukemia cell lines to differentiate into dendritic cells", Oncol. Lett., Oct. 2012, 4(4): 595-600.
Gupta et al., "Role of CA125 in predicting ovarian cancer survival—a review of the epidemiological literature", J. Ovarian Res., Oct. 9, 2009, 2(13): 1-20.

(56) References Cited

OTHER PUBLICATIONS

International Search Report and Written Opinion for PCT International Patent Application No. PCT/IB2023/052272 mailed Jun. 21, 2023.
International Search Report and Written Opinion for PCT International Patent Application No. PCT/IB2023/054997, mailed Aug. 11, 2023.
International Search Report and Written Opinion for PCT International Patent Application No. PCT/IB2023/061000 mailed Jan. 24, 2023.
Ji et al., "Aberrant expression of CD133 and CD82 in patients with pediatric acute lymphoblastic leukemia and the clinical significance", Oncol Lett, Nov. 2017, 14(5): 5811-5818.
Koeffler, "Induction of differentiation of human acute myelogenous leukemia cells: therapeutic implications", Blood, Oct. 1983, 62(4): 709-721.
Laurenti et al., "From haematopoietic stem cells to complex differentiation landscapes", Nature, 2018, 553(7689): 418-426.
Ning et al., "A Rapid Culture Technique Produces Functional Dendritic-Like Cells from Human Acute Myeloid Leukemia Cell Lines", J. Biomed. Biotechnol., 2011, 172965: 1-10.
Nobuoka et al., "Intratumoral peptide injection enhances tumor cell antigenicity recognized by cytotoxic T lymphocytes: a potential option for improvement in antigen-specific cancer immunotherapy", Cancer Immunol Immunother., Apr. 2013, 62(4): 639-652.
Sikic et al., "First-in-Human, First-in-Class Phase I Trial of the Anti-CD47 Antibody Hu5F9-G4 in Patients With Advanced Cancers", J Clin Oncol., Apr. 20, 2019, 37(12): 946-953.
Skopek et al., "Choosing the Right Cell Line for Acute Myeloid Leukemia (AML) Research", Int J Mol Sci., 2023, 24(5377): 1-34.
Tanaka et al., "Recent progress in and challenges in cellular therapy using NK cells for hematological malignancies", Blood Reviews, Mar. 20, 2020, 44: 100678.
Trivedi et al., "Generation of CMV-specific T lymphocytes using protein-spanning pools of pp65-derived overlapping pentadecapeptides for adoptive immunotherapy", Blood, 2005, 105(7): 2793-2801.
Van De Loosdrecht et al., "Clinical Study Protocol an International Multicentre, Open-Label Study to Evaluate the Efficacy and Safety of Two Different Vaccination Regimens of Immunotherapy with Allogeneic Dendritic Cells, DCP-001, In Patients with Acute Myeloid Leukaemia (ADVANCE-II)", Aug. 27, 2018, CT Identifier: NCT03697707.
Van De Loosdrecht et al., "Use of an Allogeneic Leukemia-Derived Dendritic Cell Vaccine in MRD+ AML-Patients Results in MRD Conversion, Improved Relapse-Free Survival and Vaccine Induced Immune Responses to Tumor Antigens", Blood, Nov. 15, 2022, 140(Suppl. 1): 1714-1715.
Van De Loosdrecht et al., "Conversion from MRD Positive to Negative Status in AML Patients in CR1 after Treatment with an Allogenic Leukemia-Derived Dendritic Cell Vaccine", Blood, Nov. 5, 2020, 136(1): 13-14.
Yan et al., "Combining Immune Checkpoint Inhibitors with Conventional Cancer Therapy", Frontiers in Immunology, Jul. 2018, vol. 9, Article 1739.
Zhou et al., "LPS-treated bone marrow-derived dendritic cells induce immune tolerance through modulating differentiation of CD4+ regulatory T cell subpopulations mediated by 3G11 and CD127", Immunologic Research, 2017, 65(3): 630-638.
Zuo et al., "386- Efficient ex-vivo expansion of adaptive NKG2C+/CD57+ NK cells from CMV-positive donors using dendritic cells derived from the acute myeloid cell line DCOne", Journal for Immuno Therapy of Cancer, Nov. 2022, 10(Suppl. 2): A407.
Awate et al., "Mechanisms of action of adjuvants", Frontiers in Immunology, 4(114):1-10 (2013).
Bender et al., "Inactivated Influenza Virus, when Presented on Dendritic Cells, Elicits Human CD8+ Cytolytic T Cell Responses", J. Exp. Med. 182:1663-1671 (1995).
Bennett et al., "Help for cytotoxic-T-cell responses is mediated by CD40 signalling", Nature, 393:478-480 (1998).
Guba, et al., "Rapamycin inhibits primary and metastatic tumor growth by antiangiogenesis: involvement of vascular endothelial growth factor", Nature Medicine 8(2):128-135 (2002).
Himanen et al., "Crystal structure of an Eph receptor-ephrin complex", Nature 414(6866):933-938 (2001).
International Search Report and Written Opinion for International Application No. PCT/IB2022/050555, mailed Apr. 20, 2022, 16 pages.
Kalinski et al., "Consensual immunity: success-driven development of T-helper-1 and T-helper-2 responses", Nature Review 5:251-260 (2005).
Leaf et al., "DCOne as an Allogeneic Cell-based Vaccine for Multiple Myeloma", Journal of Immunotherapy 40(9):315-322 (2017).
Montfoort et al., "NKG2A Blockade Potentiates CD8 T Cell Immunity Induced by Cancer Vaccines", Cell 175(7):1744-1755 (2018).
Nagasawa et al., "Preclinical studies support therapeutic application of the leukemic cell-based cancer relapse vaccine DCP-001 in ovarian cancer", Journal for Immunotherapy Cancer 8(Suppl. 3): A102-A103 (Abstract 171) (2020).
Pashine et al., "Targeting the innate immune response with improved vaccine adjuvants", Nature Medicine Supplement 11(4): S63-S68 (2005).
Popkov et al., "Human/mouse cross-reactive anti-VEGF receptor 2 recombinant antibodies selected from an immune b9 allotype rabbit antibody library", Journal of Immunological Methods 288:149-164 (2004).
Presta et al., "Humanization of an Anti-Vascular Endothelial Growth Factor Monoclonal Antibody for the Therapy of Solid Tumors and Other Disorders", Cancer Research 57:4593-4599 (1997).
Sommandas et al., "Novel vaccination strategies using tumour-independent antigens to induce anti-tumour immunity in solid tumours", https://dcprime.com/wp-content/uploads/2018/07/Poster-FINAL-DCprime_SITC2019-NOV2019.pdf [retrieved on Apr. 4, 2022] poster.
Temizoz et al., "Vaccine adjuvants as potential cancer immunotherapeutics", International Immunology 28(7):329-338 (2016).
Van De Loosdrecht et al., "A novel allogeneic off-the-shelf dendritic cell vaccine for post-remission treatment of elderly patients with acute myeloid leukemia", Cancer Immunology, Immunotherapy 67(10):1505-1518 (2018).
Wallgren et al., "Direction Allorecognition Promotes Activation of Bystander Dendritic Cells and Licenses Them for TH1 Priming: A Functional Link Between Direct and Indirect Allosensitization", Scandinavian Journal of Immunology 62:234-242 (2005).
Fellermann et al., "Super-resolution microscopy unveils transmembrane domain-mediated internalization of cross-reacting material 197 into diphtheria toxin-resistant mouse J774A.1 cells and primary rat fibroblasts in vitro", Arch Toxicol., May 2020, 94(5): 1753-1761.
Schmid, "A nostalgic look back 40 years after the discovery of receptor-mediated endocytosis", Mol Biol Cell., Jan. 1, 2019, 30(1): 1-3.
Wang et al., "Diphtheria toxin mutant CRM197-mediated transcytosis across blood-brain barrier in vitro", Cell Mol Neurobiol., Jul. 2010, 30(5): 717-725, Epublished Jan. 16, 2010.
Zhang et al., "The Multiple Functions of HB-EGF in Female Reproduction and Related Cancer: Molecular Mechanisms and Targeting Strategies", Reprod Sci., Sep. 2024, 31(9): 2588-2603, Epublished Feb. 29, 2024.

\* cited by examiner

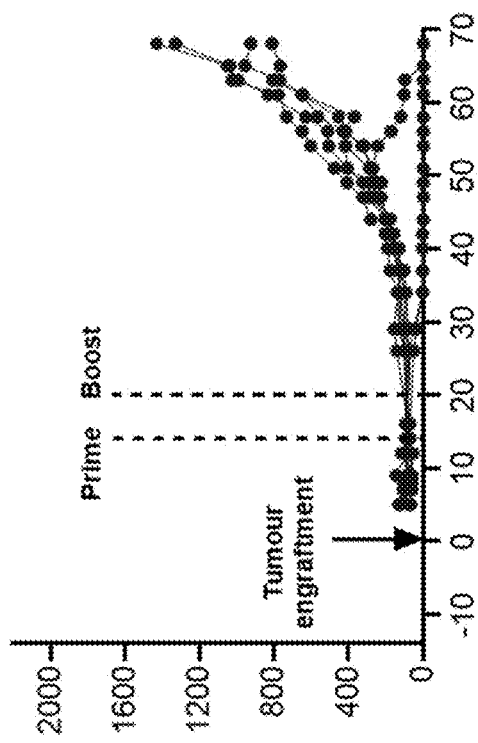
FIG. 4A
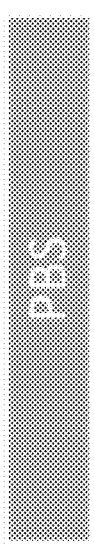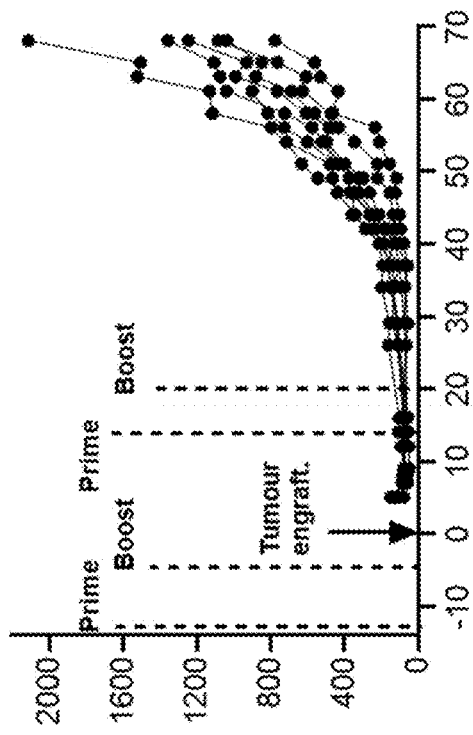
FIG. 4B

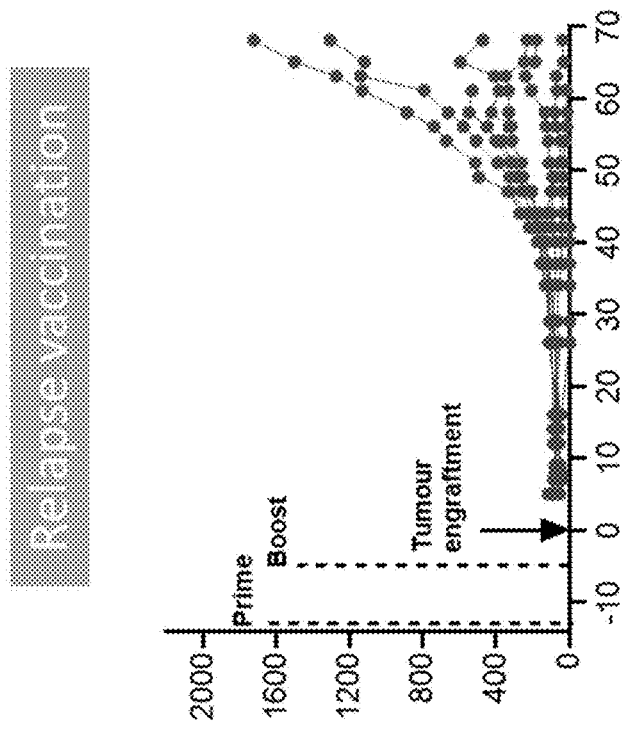

METHODS OF TUMOR VACCINATION

RELATED APPLICATIONS

This application claims the benefit of U.S. Provisional Application No. 63/140,617, filed on Jan. 22, 2021, which is incorporated by reference in its entirety for all purposes.

BACKGROUND

Traditionally, and currently still, the focus in therapeutic tumor vaccines is on vaccination with tumor antigens, which are processed by antigen-presenting cells (APC's) such as dendritic cells (DCs) to thereby provide for T cell activation and the mounting of an immune response against the tumor. The goal of such a vaccination strategy is to enlarge the pool of tumor-specific T-cells from the naïve repertoire, but also to reverse tumor-associated dormancy or anergy through the presentation of tumor antigens, in an effort to break central tolerance to those antigens and to overcome blunting of the $CD4^+$ and/or $CD8^+$ T cell repertoire.

Immunotherapies have revolutionized the cancer therapy landscape. One barrier to effective immunotherapy lies in the propensity of the tumor to evade immune control by altering itself to reduce expression of the tumor antigens or by creating an environment (the tumor micro-environment or TME) that is inhibitory for T cells and other cells of the immune system. In this way, T cell repertoires that recognize tumor antigens are inactivated, leading to inert or exhausted T cell populations. A specific class of cancer immunotherapies are dendritic-cell based vaccines comprising autologous or allogeneic dendritic cells combined with one or more tumor-associated antigens. Current vaccination approaches include the administration of vaccines at sites away from the tumor, e.g., via intradermal or intranodal injection, or the injection of vaccines directly into the tumor microenvironment. However, many vaccination approaches are circumvented by the immune-evasive properties of tumor cells because the natural selection pressure on the tumor is generally not strong enough to force the tumor into cell death.

Accordingly, there is a need for improved vaccination strategies.

SUMMARY

Provided herein is a combination vaccination strategy that exhibits superior efficacy to conventional vaccination approaches. In a first aspect, the vaccination strategy of the present disclosure comprises one or more intratumoral administration steps, wherein each of the one or more intratumoral administration steps comprises administering an effective amount of a first composition (e.g., a first immunogenic vaccine composition) to a tumor site. In a second aspect, the vaccination strategy of the present disclosure comprises one or more vaccination steps, wherein each of the one or more vaccination steps comprises administering an effective amount of a second composition (e.g., a second immunogenic vaccine composition) to a site distal to the tumor site. In certain embodiments, the present disclosure is based on the finding that a combination vaccination strategy comprising administering one or more compositions (e.g., immunogenic vaccine compositions) intratumorally at a tumor site, and extra-tumorally at a site distal to the tumor site, results in a stronger reduction of tumor growth as compared to intratumoral or extra-tumoral administrations of the compositions alone.

In one aspect, a method for treating a tumor in a subject in need thereof, comprising: one or more intratumoral administration steps each comprising administering to the subject at a tumor site, an effective amount of a first composition comprising an allogeneic leukemia-derived cell; and one or more vaccination steps each comprising administering to the subject at a site distal to the tumor site, an effective amount of a second composition comprising an allogeneic leukemia-derived cell, is provided.

In certain exemplary embodiments, the one or more intratumoral administration steps each comprises administering the first composition into the tumor or at a site proximal to the tumor. In certain exemplary embodiments, the site proximal to the tumor is peritumoral. In certain exemplary embodiments, the first composition is prepared for intratumoral administration. In certain exemplary embodiments, the first composition comprises a diluent or solvent acceptable for intratumoral administration.

In certain exemplary embodiments, the one or more vaccination steps each comprise administering the second composition via a route selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue. In certain exemplary embodiments, the one or more vaccination steps each comprise intravenously administering the second composition. In certain exemplary embodiments, the second composition is prepared for intravenous administration. In certain exemplary embodiments, the second composition comprises a diluent or solvent acceptable for intravenous administration. In certain exemplary embodiments, the one or more vaccination steps each comprise intradermally administering the second composition. In certain exemplary embodiments, the second composition is prepared for intradermal administration. In certain exemplary embodiments, the second composition comprises a diluent or solvent acceptable for intradermal administration. In certain exemplary embodiments, the one or more vaccination steps each comprise intramuscularly administering the second composition. In certain exemplary embodiments, the second composition is prepared for intramuscular administration. In certain exemplary embodiments, the second composition comprises a diluent or solvent acceptable for intramuscular administration.

In certain exemplary embodiments, the one or more vaccination steps each comprise administering the second composition into an organ system that is different than the organ system in which the tumor resides. In certain exemplary embodiments, the one or more vaccination steps each comprise administering the second composition at a site contralateral to the tumor.

In certain exemplary embodiments, the one or more intratumoral administration steps are performed before the one or more vaccination steps. In certain exemplary embodiments, the one or more intratumoral administration steps are performed after the one or more vaccination steps.

In certain exemplary embodiments, the method further comprises one or more vaccination steps following the one or more intratumoral administration steps. In certain exemplary embodiments, the one or more vaccination steps following the one or more intratumoral administration steps each comprise administering to the subject an effective amount of a third composition comprising an allogeneic leukemia-derived cell via a route selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue. In certain exemplary embodiments, the one or more vaccination steps following the one or more intratumoral administration steps are administered via the same route as the one or more vaccination steps. In certain exemplary embodiments, the one or more vaccination steps following the one or more intratumoral administration steps are administered via a different route as the one or more vaccination steps.

In certain exemplary embodiments, the time between the one or more intratumoral administration steps and the one or more vaccination steps is sufficient for an immune response to be mounted as a result of the one or more vaccination steps. In certain exemplary embodiments, the time between the one or more intratumoral administration steps and the one or more vaccination steps is sufficient for an immune response to be mounted as a result of the first vaccination step of the one or more vaccination steps. In certain exemplary embodiments, the time between the one or more intratumoral administration steps and the one or more vaccination steps is about 2 days to about 21 days.

In certain exemplary embodiments, the one or more intratumoral administration steps are performed at substantially the same time as the one or more vaccination steps. In certain exemplary embodiments, the one or more intratumoral administration steps are performed at substantially the same time as the first vaccination step of the one or more vaccination steps. In certain exemplary embodiments, the one or more intratumoral administration steps are performed on the same day as the one or more vaccination steps. In certain exemplary embodiments, the one or more intratumoral administration steps are performed on the same day as the first vaccination step of the one or more vaccination steps.

In certain exemplary embodiments, the time between the one or more vaccination steps following the one or more intratumoral administration steps, and the one or more intratumoral administration steps is sufficient for an immune response to be mounted as a result of the first vaccination step of the one or more vaccination steps. In certain exemplary embodiments, the time between the one or more vaccination steps following the one or more intratumoral administration steps, and the one or more intratumoral administration steps is about 2 days to about 21 days. In certain exemplary embodiments, the one or more vaccination steps following the one or more intratumoral administration steps, and the one or more intratumoral administration steps are performed at substantially the same time. In certain exemplary embodiments, the first of the one or more vaccination steps following the one or more intratumoral administration steps is performed at substantially the same time as the one or more intratumoral administration steps. In certain exemplary embodiments, the one or more vaccination steps following the one or more intratumoral administration steps are performed on the same day as the one or more intratumoral administration steps. In certain exemplary embodiments, the first of the one or more vaccination steps following the one or more intratumoral administration steps is performed on the same day as the first of the one or more intratumoral administration steps.

In certain exemplary embodiments, the allogeneic leukemia-derived cell comprises at least one tumor associated antigen or a nucleic acid encoding at least one tumor associated antigen that is associated with the tumor in the subject. In certain exemplary embodiments, the allogeneic leukemia-derived cell comprises at least one tumor associated antigen or a nucleic acid encoding at least one tumor associated antigen that is not associated with the tumor in the subject. In certain exemplary embodiments, the allogeneic leukemia-derived cell comprises at least one tumor associated antigen or a nucleic acid encoding at least one tumor associated antigen, wherein the tumor associated antigen is selected from the group consisting of WT-1, MUC-1, RHAMM, PRAME, p53, and Survivin. In certain exemplary embodiments, the allogeneic leukemia-derived cell comprises WT-1, MUC-1, PRAME, and Survivin. In certain exemplary embodiments, the allogeneic leukemia-derived cell comprises a dendritic cell phenotype. In certain exemplary embodiments, the allogeneic leukemia-derived cell comprises a mature dendritic cell phenotype. In certain exemplary embodiments, the allogeneic leukemia-derived cell comprises a genetic aberration between chromosome 11p15.5 to 11p12. In certain exemplary embodiments, the genetic aberration encompasses about 16 Mb of genomic regions. In certain exemplary embodiments, the allogeneic leukemia-derived cell is CD34-positive, CD1a-positive, and CD83-positive. In certain exemplary embodiments, the allogeneic leukemia-derived cell expresses a cell surface marker selected from the group consisting of DC-SIGN, Langerin, CD80, CD86, CD70, CD40, and any combination thereof. In certain exemplary embodiments, the allogeneic leukemia-derived cell is CD34-positive, CD1a-positive, CD83-positive, CD80-positive, CD86-positive, and CD40-positive. In certain exemplary embodiments, the allogeneic leukemia-derived cell is CD14-negative. In certain exemplary embodiments, the allogeneic leukemia-derived cell is derived from the DCOne cell line. In certain exemplary embodiments, the allogeneic leukemia-derived cell has been inactivated. In certain exemplary embodiments, the allogeneic leukemia-derived cell has been inactivated via irradiation.

In certain exemplary embodiments, the first composition optionally further comprises one or more pharmaceutically-acceptable carriers, adjuvants, excipients and/or diluents. In certain exemplary embodiments, the second composition optionally further comprises one or more pharmaceutically-acceptable carriers, adjuvants, excipients and/or diluents. In certain exemplary embodiments, the third composition optionally further comprises one or more pharmaceutically-acceptable carriers, adjuvants, excipients and/or diluents.

In certain exemplary embodiments, the subject has previously suffered from the tumor. In certain exemplary embodiments, the subject has previously received treatment for the tumor. In certain exemplary embodiments, the subject is suffering from relapse of the tumor. In certain exemplary embodiments, the subject is a human.

In certain exemplary embodiments, the subject is a domesticated animal and/or an animal suitable for veterinary healthcare.

In certain exemplary embodiments, the tumor is a solid tumor. In certain exemplary embodiments, the solid tumor is selected from the group consisting of a sarcoma, a carcinoma, and a lymphoma. In certain exemplary embodiments, the solid tumor is ovarian cancer. In certain exemplary embodiments, the solid tumor is a melanoma.

BRIEF DESCRIPTION OF THE DRAWINGS

FIGS. 4A-4C depicts graphs showing the tumor volume (in mm$^3$) measured over time in SKOV3 tumor engrafted mice administered control vaccination (PBS; FIG. 4A); combination vaccination (DCP-001 IP+IT; FIG. 4B); and relapse vaccination (FIG. 4C).

DETAILED DESCRIPTION

Figure 1:
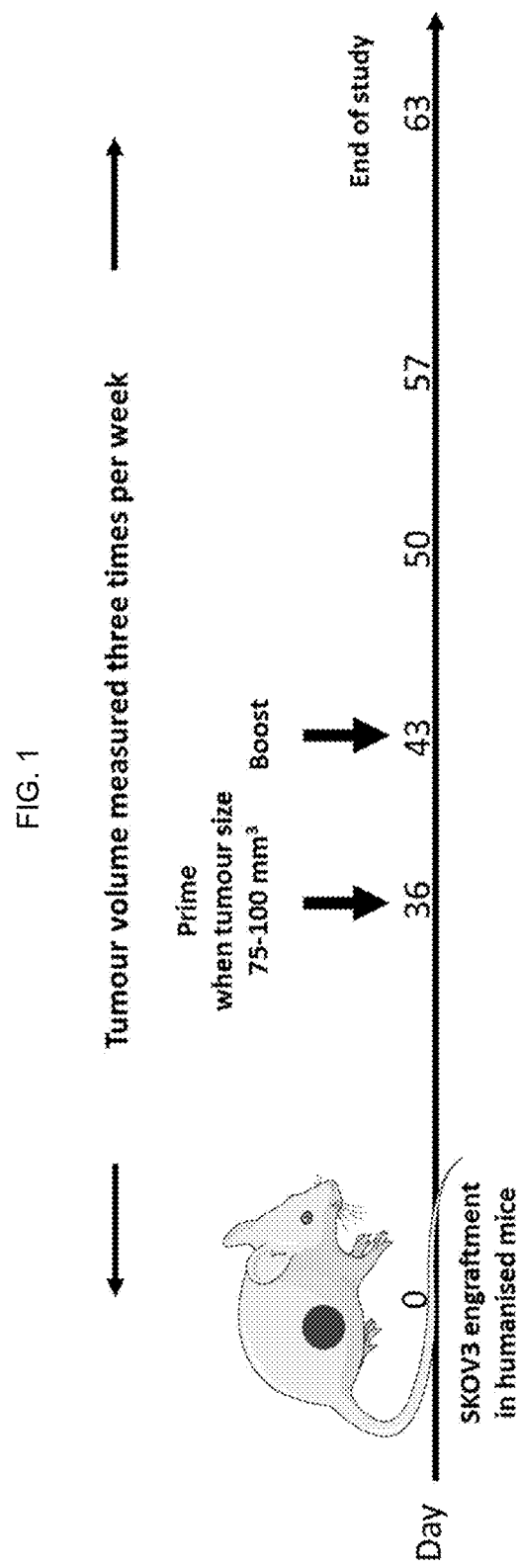
FIG. 1 depicts a schematic showing a vaccination strategy of an SKOV3 engrafted ovarian cancer mouse model, according to one embodiment.

Provided herein are methods for generating an immune response against a tumor in a subject. In certain embodiments, the generated immune response is sufficient for treating the tumor in the subject. The methods generally comprise one or more intratumoral administration steps each comprising administering to the subject at a tumor site, an effective amount of a first composition (e.g., a first immunogenic vaccine composition); and one or more vaccination steps each comprising administering to the subject at a site distal to the tumor site, an effective amount of a second composition (e.g., a second immunogenic vaccine composition).

It is to be understood that the methods described herein are not limited to particular methods and experimental conditions disclosed herein as such methods and conditions may vary. It is also to be understood that the terminology used herein is for the purpose of describing particular embodiments only, and is not intended to be limiting. The methods described herein use conventional molecular and cellular biological and immunological techniques that are well within the skill of the ordinary artisan. Such techniques are well known to the skilled artisan and are explained in the scientific literature.

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, ±5%, ±1%, or ±0.1% from the specified value, as such variations are appropriate to perform the disclosed methods.

As used herein, to "alleviate" a disease means reducing the severity of one or more symptoms of the disease.

As used herein, the term "autologous" is meant to refer to any material derived from the same individual to which it is later to be re-introduced into the individual. As used herein, the term "allogeneic" refers to the involvement of living tissues or cells that are genetically dissimilar and hence immunologically incompatible, with respect to a subject in need of treatment. While genetically dissimilar, an allogeneic cell, e.g., an allogeneic leukemia-derived cell described herein, is derived from the same species. For example, a method described herein comprising administering to a subject an allogeneic leukemia-derived cell, refers to the administration of an leukemia-derived cell that is genetically dissimilar to the subject, albeit still of the same species.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

As used herein "endogenous" refers to any material from or produced inside an organism, cell, tissue or system.

"Parenteral" administration of an immunogenic composition includes, e.g., subcutaneous (s.c.), intravenous (i.v.), intramuscular (i.m.), or intrasternal injection, or infusion techniques.

The term "therapeutic" as used herein means a treatment and/or prophylaxis. A therapeutic effect is obtained by suppression, remission, or eradication of a disease state.

To "treat" a disease as the term is used herein, means to reduce the frequency or severity of at least one sign or symptom of a disease or disorder experienced by a subject.

The term "immune response," as used herein, includes T-cell mediated and/or B-cell mediated immune responses. Exemplary immune functions of T cells include, e.g., cytokine production and induction of cytotoxicity in other cells. B-cell functions include antibody production. In addition, the term includes immune responses that are indirectly affected by T-cell activation, e.g., antibody production and activation of cytokine responsive cells, e.g., macrophages. Immune cells involved in the immune response include lymphocytes, such as B cells and T cells ($CD4^+$ and $CD8^+$ cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes. In certain embodiments, the term immune response refers to a T-cell mediated immune response. The immune response may in some embodiments be a T cell-dependent immune response.

The term "T-cell dependent immune response," as used herein, refers to an immune response wherein either T-cells, B-cells or both T- and B-cell populations are activated, and wherein T-cells further assist T and B cells and other immune cells in executing their function.

The term "T-cell mediated immune response," as used herein, refers to an immune response that is T-cell driven, and where elicitation of another or further immune response is dependent on activation of T-cells. In certain embodiments, the immune response is a T-cell mediated immune response/T-cell dependent immune response. The skilled person is well aware of methods and means for mounting a T-cell mediated immune response/T-cell dependent immune response, for instance through selection of an appropriate antigen to which measurable T cell responses have been documented, or by selecting an appropriate adjuvant or carrier such as a chemical adjuvant, biological adjuvant, protein, viral vaccine, dendritic cell vaccine or any other composition that can be administered as a vaccine composition (Bender et al., *J. Exp. Med*, 182:1663-1671 (1995); Bennett et al., *Nature*, 393:478-480 (1998); Kalinski and Moser, *Nature*, 5:251-260 (2005); Pashine et al., *Nature Medicine Supplement*, 11:S63-S68 (2005), the disclosures of which are incorporated by reference herein in their entireties).

The term "tumor," as used herein, includes reference to cellular material, e.g., a tissue, proliferating at an abnormally high rate. A growth comprising neoplastic cells is a neoplasm, also known as a "tumor," and generally forms a distinct tissue mass in a body of a subject. A tumor may show partial or total lack of structural organization and functional coordination with the normal tissue. As used herein, a tumor is intended to encompass hematopoietic tumors as well as solid tumors. In certain embodiments, the tumor is a solid tumor. The term tumor includes reference to the tumor micro-environment or tumor site, i.e., the area within the tumor and the area directly outside the tumorous tissue. In certain embodiments, the tumor micro-environment or tumor site includes an area within the boundaries of the tumor tissue. In certain embodiments, the tumor micro-environment or tumor site includes the tumor interstitial compartment of a tumor, which is defined herein as all that is interposed between the plasma membrane of neoplastic cells and the vascular wall of the newly formed neovessels.

As used herein, the terms "tumor microenvironment" or "tumor site" refers to a location within a subject in which a tumor resides, including the area immediately surrounding the tumor. The area immediately surrounding the tumor can be referred to as the peritumoral area.

A tumor may be benign (e.g., a benign tumor) or malignant (e.g., a malignant tumor or cancer). Malignant tumors can be broadly classified into three major types: those arising from epithelial structures are called carcinomas, those that originate from connective tissues such as muscle, cartilage, fat or bone are called sarcomas, and those affecting hematopoietic structures (structures pertaining to the formation of blood cells) including components of the immune system, are called leukemias and lymphomas. Other tumors include, but are not limited to, neurofibromatosis. In certain embodiments, the tumor is an ovarian cancer (e.g., an epithelial ovarian cancer, which can be further subtyped into a serous, a clear cell, an endometrioid, a mucinous, or a mixed epithelial ovarian cancer). In certain embodiments, the tumor is a melanoma.

Solid tumors are abnormal masses of tissue that can be benign or malignant. In certain embodiments, solid tumors are named for the type of cells that form them (such as sarcomas, carcinomas, and lymphomas). Examples of solid tumors that can be amenable to therapy by a method disclosed herein, such as sarcomas and carcinomas, include, but are not limited to, liposarcoma, fibrosarcoma, chondrosarcoma, osteosarcoma, myxosarcoma, and other sarcomas, mesothelioma, synovioma, leiomyosarcoma, Ewing's tumor, colon carcinoma, rhabdomyosarcoma, pancreatic cancer, lymphoid malignancy, lung cancers, breast cancer, prostate cancer, ovarian cancer, hepatocellular carcinoma, adenocarcinoma, basal cell carcinoma, sweat gland carcinoma, squamous cell carcinoma, medullary thyroid carcinoma, pheochromocytomas sebaceous gland carcinoma, papillary thyroid carcinoma, papillary adenocarcinomas, papillary carcinoma, medullary carcinoma, bronchogenic carcinoma, hepatoma, renal cell carcinoma, bile duct carcinoma, Wilms' tumor, choriocarcinoma, cervical cancer, seminoma, testicular tumor, bladder carcinoma, melanoma, CNS tumors (e.g., a glioma, e.g., brainstem glioma and mixed gliomas, glioblastoma (e.g., glioblastoma multiforme), germinoma, astrocytoma, craniopharyngioma, medulloblastoma, ependymoma, Schwannoma, CNS lymphoma, acoustic neuroma, pinealoma, hemangioblastoma, meningioma, oligodendroglioma, retinoblastoma, neuroblastoma, and brain metastases), and the like.

Carcinomas that can be amenable to therapy by a method disclosed herein include, but are not limited to, squamous cell carcinoma (various tissues), basal cell carcinoma (a form of skin cancer), esophageal carcinoma, bladder carcinoma, including transitional cell carcinoma (a malignant neoplasm of the bladder), hepatocellular carcinoma, colorectal carcinoma, bronchogenic carcinoma, lung carcinoma, including small cell carcinoma and non-small cell carcinoma of the lung, colon carcinoma, thyroid carcinoma, gastric carcinoma, breast carcinoma, ovarian carcinoma, adrenocortical carcinoma, pancreatic carcinoma, sweat gland carcinoma, prostate carcinoma, papillary carcinoma, adenocarcinoma, sebaceous gland carcinoma, medullary carcinoma, papillary adenocarcinoma, ductal carcinoma in situ or bile duct carcinoma, cystadenocarcinoma, renal cell carcinoma, choriocarcinoma, Wilm's tumor, seminoma, embryonal carcinoma, cervical carcinoma, testicular carcinoma, nasopharyngeal carcinoma, osteogenic carcinoma, epithelial carcinoma, uterine carcinoma, and the like.

Sarcomas that can be amenable to therapy by a method disclosed herein include, but are not limited to, myxosarcoma, chondrosarcoma, chordoma, osteogenic sarcoma, liposarcoma, fibrosarcoma, angiosarcoma, lymphangiosarcoma, endotheliosarcoma, osteosarcoma, mesothelioma, Ewing's sarcoma, leiomyosarcoma, rhabdomyosarcoma, lymphangioendotheliosarcoma, synovioma, and other soft tissue sarcomas.

The term "subject," as used herein, refers to the recipient of a method as described herein, i.e., a recipient that can mount a cellular immune response, for example, a mammal. In certain embodiments, the subject is a human. In certain embodiments, the subject is a domesticated animal, e.g., a horse, a cow, a pig, a sheep, a dog, a cat, etc. In certain embodiments, the subject is an animal suitable for veterinary healthcare, e.g., a zoo animal. The terms "patient" and "subject" may be used interchangeably herein. In certain embodiments, the subject is a human suffering from a tumor (e.g., a solid tumor). In certain embodiments, the subject is a human who has previously suffered from a tumor, and/or has previously received treatment for a tumor. Such a subject could be suffering from relapse of the tumor. Accordingly, a suitable subject includes one that is suffering from relapse of a tumor. In certain embodiments, the subject is a domesticated animal suffering from a tumor (e.g., a solid tumor). In certain embodiments, the subject is an animal suitable for veterinary healthcare suffering from a tumor (e.g., a solid tumor). As used herein, an "animal suitable for veterinary healthcare" is any animal that is suitable for treatment by a veterinarian, and includes, without limitation, wild animals, domesticated animals, and zoo animals that are capable of mounting a cellular immune response.

The term "immunogenic composition," as used herein, refers to a substance which induces a specific immune response against an immunogen in a subject who is in need of an immune response against said immunogen. The composition may include an adjuvant and optionally one or more pharmaceutically-acceptable carriers, excipients and/or diluents. The immunogenic composition can be employed in one or more vaccination steps as described herein, such as at least 2, 3, 4 or at least 5 vaccinations separated in time. In certain embodiments, the immunogenic composition comprises an allogeneic leukemia-derived cell. In certain embodiments, the immunogenic composition is used in the one or more vaccination steps (in an immunogenic composition such as a vaccine composition) and/or the intratumoral administration step as described herein.

The term "intratumoral," as used herein, refers to delivery or transport of an immunogen (e.g., a composition comprising an allogeneic leukemia-derived cell) into a tumor. One example of intratumoral delivery, or transport, of a composition as described herein is by intratumoral administration, a route of administration that is generally known in the art.

The phrase "prepared for intratumoral delivery," as used herein, refers to a composition as described herein, that is adapted for intratumoral delivery and/or is in a formulation that allows for intratumoral delivery. The preparation used for intratumoral delivery may be composed such that it has a beneficial effect on the interaction between the immune system and the tumor. In certain embodiments, intratumoral administration of a composition (e.g., comprising a dendritic cell or a cell having dendritic cell qualities, e.g., an allogeneic leukemia-derived cell described herein) may provide for additional immune stimulation via direct interaction with T cells entering the tumor and/or indirectly by recruiting bystander antigen-presenting cells (Laurell et al., *Journal for Immunotherapy of Cancer*, 5:52 (2017); Wallgren et al., *Scandinavian Journal of Immunology*, 62, p. 234-242 (2005), the disclosures of which are incorporated by reference herein in their entireties). The skilled person is well aware of the various methods and means for preparing a composition for intratumoral delivery.

As used herein, the term "intratumoral administration step" refers to the active manipulation of the antigenic state of a tumor by intratumoral delivery of a composition as described herein. One or more intratumoral administration steps may be performed, wherein each intratumoral administration step comprises administering a composition intratumorally. In certain embodiments, the intratumoral administration step(s) provides for (i) intracellular delivery and subsequent processing and presentation of an immunogen by a non-tumor cell in said tumor; or (ii) extracellular delivery of an immunogen to the tumor (i.e., extracellular to the cells present in said tumor before intratumoral administration of the composition), e.g., by using an allogeneic leukemia-derived cell that comprises an immunogen. An intratumoral administration step when referring to a step in a method (e.g., a vaccination strategy) as described herein, refers to the administering of an effective amount of a composition (e.g., comprising an allogeneic leukemia-derived cell) to a subject at a tumor site.

As used herein, the term "vaccination step" refers to a step in a method (e.g., a vaccination strategy) as described herein, wherein an effective amount of a composition (e.g., comprising an allogeneic leukemia-derived cell) is administered to a subject at a site distal to a tumor site. In certain embodiments, in a vaccination step of a method as described herein, the composition is administered at a site that is not the site in which the tumor resides (e.g., not the tumor site). In certain embodiments, in a vaccination step of a method as described herein, the composition is administered at an extra-tumoral site. One or more vaccination steps may be performed, wherein each vaccination step comprises administering the composition at a site distal to a tumor site. The purpose of more than one vaccination step may be to enhance the immune response to the immunogen. For example, in certain embodiments, a first vaccination step is performed, followed by one or more subsequent vaccination steps that are performed as an immune response against the immunogen is being mounted as a result of the first vaccination step.

As used herein, the term "extra-tumoral" refers to a location, e.g., in the body of a subject, that is away (e.g., distal) from a tumor and immediately surrounding tissue (e.g., that may make up the tumor microenvironment).

It is readily appreciated by the skilled artisan that: (i) the composition used in an intratumoral administration step of a method described herein, prepared for intratumoral delivery as described herein; and (ii) the compositions of the one or more vaccination steps of a method described herein, comprises immunogens (e.g., an allogeneic leukemia-derived cell) that are matched, and when administered, elicits an immune response that is directed against one or more (target) epitopes established by that immunogen. Thus, in certain embodiments, the immunogens under (i) and (ii) are immunologically matched in that a T-cell epitope and/or a B-cell epitope of the immunogen in a tumor are recognized by, or are reactive with, a T-cell and/or B-cell response elicited by the immunogen.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Allogeneic Leukemia-Derived Cells

Provided herein are methods for eliciting an immune response against a tumor, thereby treating the tumor, in a subject in need. Aspects of the methods described herein comprise: (i) one or more intratumoral administration steps each comprising administering to the subject at a tumor site, an effective amount of a first composition; and (ii) one or more vaccination steps each comprising administering to the subject at a site distal to the tumor site, an effective amount of a second composition. While the present disclosure provides methods where the intratumoral administration step occurs before or after the one or more vaccination steps, when the one or more vaccination steps occur before the intratumoral administration step, methods provided herein also include wherein one or more vaccination steps occur following the intratumoral administration step. In such cases, the method comprises: (i) one or more vaccination steps each comprising administering to the subject at a site distal to the tumor site, an effective amount of a first composition; (ii) an intratumoral administration step comprising administering to the subject at a tumor site, an effective amount of a second composition; and (iii) one or more vaccination steps following the intratumoral administration step, each comprising administering an effective amount of a third composition.

It will readily be appreciated by those of ordinary skill in the art that the methods (e.g., vaccination strategies) provided herein for eliciting an immune response against, and/or treating a tumor, can employ the use of any immunogenic compositions. In certain embodiments, the first, second, and/or third compositions each comprise an allogeneic leukemia-derived cell. As used herein, the term "leukemia-derived cell" refers to a cell of leukemic origin that is capable of presenting an antigen, or an immunogenic portion thereof, together with an MHC class I complex or MHC class II complex. The term "allogeneic leukemia-derived cell" refers to a leukemia-derived cell that is genetically dissimilar with respect to the subject it is utilized to treat, yet is of the same species.

In some embodiments, an allogeneic leukemia-derived cell provided herein comprises a dendritic cell phenotype. In some embodiments, an allogeneic leukemia-derived cell provided herein comprises a mature dendritic cell phenotype. The term "dendritic cell," as used herein, refers to a professional antigen presenting cell (APC) that can take up an antigen, and is capable of presenting the antigen, or an immunogenic portion thereof, together with an MHC class I complex or MHC class II complex. In some embodiments, an allogeneic leukemia-derived cell as described herein has a mature dendritic cell phenotype capable of performing similar functions to those of a mature dendritic cell. The term dendritic cell includes both immature dendritic cells ("imDC") and mature dendritic cells ("mDC"), depending on maturity.

In certain embodiments, the allogeneic leukemia-derived cell is a cell derived from cell line DCOne as deposited under the conditions of the Budapest treaty with the DSMZ under accession number DSMZ ACC3189 on 15 Nov. 2012. The process of obtaining mature cells from the deposited DCOne cell line is for instance described in EP2931878B1, the disclosure of which is incorporated by reference herein in its entirety. In certain embodiments, the allogeneic leukemia-derived cell of the present disclosure is a cell of cell line DCOne as described in PCT Publication Nos. WO 2014/006058 and WO 2014/090795, the disclosures of which are incorporated by reference herein in their entireties. In certain embodiments, the allogeneic leukemia-derived cell is comprised within a vaccine called DCP-001. DCP-001 is an allogeneic off-the shelf whole cell based vaccine derived from the DCOne cell line. In one embodiment, DCP-001 is produced by culturing DCOne cells in a cocktail of GM-CSF, TNFα, and IL-4 in the presence of mitoxantrone to accelerate differentiation of cells that have a dendritic cell phenotype, followed by maturation of the cells in the presence of prostaglandin-E2, TNFα, and IL-1β.

In certain embodiments, the allogeneic leukemia-derived cell is derived from a leukemia cell. In certain embodiments, the allogeneic leukemia-derived cell is derived from a subject having leukemia (e.g., a genetically dissimilar subject with respect to the subject that the leukemia-derived cell is utilized to treat). In certain embodiments, the allogeneic leukemia-derived cell is derived from the peripheral blood of a patient having leukemia. In certain embodiments, the allogeneic leukemia-derived cell is derived from the peripheral blood of a patient having acute myeloid leukemia. The skilled artisan will recognize that an allogeneic leukemia-derived cell can be derived from any patient-obtained peripheral blood, wherein the patient has any type of leukemia, given that the leukemia-derived cell thus derived comprises the characteristics disclosed herein.

In certain embodiments, the allogeneic leukemia-derived cell is CD34-positive, CD1a-positive, and CD83-positive. In certain embodiments, the allogeneic leukemia-derived cell comprises a cell surface marker selected from the group consisting of CD14, DC-SIGN, Langerin, CD40, CD70, CD80, CD83, CD86, and any combination thereof. In certain embodiments, the allogeneic leukemia-derived cell expresses a cell surface marker selected from the group consisting of DC-SIGN, Langerin, CD40, CD70, CD80, CD83, CD86, and any combination thereof. In certain embodiments, the allogeneic leukemia-derived cell comprises an MHC class I molecule. In certain embodiments, the allogeneic leukemia-derived cell comprises an MHC class II molecule. In certain embodiments, the allogeneic leukemia-derived cell does not express CD14. Accordingly, in certain embodiments, the allogeneic leukemia-derived cell is CD34-positive, CD1a-positive, CD83-positive, CD86-positive, CD40-positive, and CD14-negative.

In certain embodiments, the allogeneic leukemia-derived cell comprises a genetic aberration between chromosome 11p15.5 to 11p12. In certain embodiments, the genetic aberration encompasses about 16 Mb of genomic regions (e.g., from about 20.7 Mb to about 36.6 Mb). In certain embodiments, the genetic aberration contains a loss of about 60 known and unknown genes.

In certain embodiments, the allogeneic leukemia-derived cell comprises a co-stimulatory molecule. In certain embodiments, the co-stimulatory molecule includes, without limitation, an MHC class I molecule, BTLA and Toll ligand receptor. Examples of co-stimulatory molecules and their ligands include, without limitation, CD27 and CD70; CD28 and CD80, CD86; 4-1BB (CD137) and 4-1BBL; OX40 and OX40L; ICOS and ICOS-L; lymphocyte function-associated antigen-1 (LFA-1) and ICAM-1; CD2 and LFA-3; CD7 and galectin-1; and the like.

In certain embodiments, the allogeneic leukemia-derived cell comprises at least one endogenous antigen. Depending on the leukemic origin of the leukemia-derived cell, the leukemia-derived cell may comprise at least one known endogenous antigen that is specific to the leukemic origin. In certain embodiments, the endogenous antigen is a tumor-associated antigen. In certain embodiments, the endogenous tumor-associated antigen may be selected from the group consisting of WT-1, RHAMM, PRAME, p53, Survivin, and MUC-1.

The allogeneic leukemia-derived cell of the present disclosure may comprise an exogenous antigen. Such an exogenous antigen may be provided to the leukemia-derived cell via various antigen loading strategies known to those skilled in the art. For example, strategies for loading an allogeneic leukemia-derived cell may include, without limitation, the use of synthetic long peptides, mRNA loading, peptide-pulsing, protein-loading, tumor lysate-loading, coculturing with a tumor cell, RNA/DNA transfection or viral transduction. Other strategies for loading an allogeneic leukemia-derived cell are known to those of skill in the art and may be used to load a leukemia-derived cell with an exogenous antigen. Generally, without being bound by any theory, the allogeneic leukemia-derived cell will process the exogenous antigen via particular molecules, e.g., via MHC I or MHC II. As such, an exogenous antigen comprised by the allogeneic leukemia-derived cell may be an MHC class I antigen or an MHC class II antigen. In certain embodiments, the exogenous antigen is a tumor-associated antigen. In certain embodiments, the exogenous antigen is associated with a disease or disorder, e.g., a non-cancer-associated disease or disorder.

In certain embodiments, the allogeneic leukemia-derived cell comprises at least one tumor associated antigen or a nucleic acid encoding at least one tumor associated antigen that is associated with the tumor in the subject. In certain embodiments, the allogeneic leukemia-derived cell comprises at least one tumor associated antigen or a nucleic acid encoding at least one tumor associated antigen that is not associated with the tumor in the subject. In certain embodiments, the allogeneic leukemia-derived cell comprises at least one tumor associated antigen or a nucleic acid encoding at least one tumor associated antigen, wherein the tumor associated antigen is selected from the group consisting of WT-1, MUC-1, RHAMM, PRAME, p53, and Survivin. In certain embodiments, the allogeneic leukemia-derived cell comprises WT-1, MUC-1, PRAME, and Survivin. In certain embodiments, the allogeneic leukemia-derived cell comprises a dendritic cell phenotype. In certain embodiments, the allogeneic leukemia-derived cell comprises a mature dendritic cell phenotype. In certain embodiments, the allogeneic leukemia-derived cell comprises a genetic aberration between chromosome 11p15.5 to 11p12. In certain embodiments, wherein the genetic aberration encompasses about 16 Mb of genomic regions. In certain embodiments, the allogeneic leukemia-derived cell is CD34-positive, CD1a-positive, and CD83-positive. In certain embodiments, the allogeneic leukemia-derived cell expresses a cell surface marker selected from the group consisting of DC-SIGN, Langerin, CD80, CD86, CD70, CD40, and any combination thereof. In certain embodiments, the allogeneic leukemia-derived cell is CD34-positive, CD1a-positive, CD83-positive, CD80-positive, CD86-positive, and CD40-positive. In certain embodiments, the allogeneic leukemia-derived cell is CD14-negative. In certain embodiments, the allogeneic leukemia-derived cell is derived from the DCOne cell line.

In certain embodiments, the allogeneic leukemia-derived cell is a cell of cell line DCOne and comprises at least one tumor associated antigen or a nucleic acid encoding at least one tumor associated antigen that is associated with the tumor in the subject. In certain embodiments, the allogeneic leukemia-derived cell is a cell of cell line DCOne and comprises at least one tumor associated antigen or a nucleic acid encoding at least one tumor associated antigen that is not associated with the tumor in the subject. In certain embodiments, the allogeneic leukemia-derived cell is a cell of cell line DCOne and comprises at least one tumor associated antigen or a nucleic acid encoding at least one tumor associated antigen, wherein the tumor associated antigen is selected from the group consisting of WT-1, MUC-1, RHAMM, PRAME, p53, and Survivin. In certain embodiments, the allogeneic leukemia-derived cell is a cell of cell line DCOne and comprises WT-1, MUC-1, PRAME, and Survivin. In certain embodiments, the allogeneic leukemia-derived cell is a cell of cell line DCOne and comprises a dendritic cell phenotype. In certain embodiments, the allogeneic leukemia-derived cell is a cell of cell line DCOne and comprises a mature dendritic cell phenotype. In certain embodiments, the allogeneic leukemia-derived cell is a cell of cell line DCOne and comprises a genetic aberration between chromosome 11p15.5 to 11p12. In certain embodiments, the allogeneic leukemia-derived cell is a cell of cell line DCOne and comprises a genetic aberration that encompasses about 16 Mb of genomic regions. In certain embodiments, the allogeneic leukemia-derived cell is a cell of cell line DCOne and is CD34-positive, CD1a-positive, and CD83-positive. In certain embodiments, the allogeneic leukemia-derived cell is a cell of cell line DCOne and expresses a cell surface marker selected from the group consisting of DC-SIGN, Langerin, CD80, CD86, CD70, CD40, and any combination thereof. In certain embodiments, the allogeneic leukemia-derived cell is a cell of cell line DCOne and is CD34-positive, CD1a-positive, CD83-positive, CD80-positive, CD86-positive, and CD40-positive. In certain embodiments, the allogeneic leukemia-derived cell is a cell of cell line DCOne and is CD14-negative.

As provided herein, certain methods utilize the use of an allogeneic leukemia-derived cell, wherein the allogeneic leukemia-derived cell is inactivated. Various methods of inactivating an allogeneic leukemia-derived cell of the present disclosure are known to those of skill in the art. In certain embodiments, the allogeneic leukemia-derived cell is irradiated. In certain embodiments, the allogeneic leukemia-derived cell is irradiated prior to its use in a method disclosed herein. Irradiation can, for example, be achieved by gamma irradiation at 30-150 Gy, e.g., 100 Gy, for a period of 1 to 3 hours, using a standard irradiation device (Gammacell or equivalent). Irradiation ensures that any remaining progenitor cell in a composition comprising the allogeneic leukemia-derived cell, e.g., a CD34 positive cell, cannot continue dividing. The cells may, for example, be irradiated prior to injection into patients, when used as a vaccine, or immediately after cultivating is stopped.

It will readily be appreciated by those of ordinary skill in the art that the methods (e.g., vaccination strategies) provided herein for eliciting an immune response against, and/or treating a tumor, can employ the use of any immunogenic compositions.

C. Pharmaceutical Compositions and Formulations

Provided herein are methods for eliciting an immune response against a tumor, and in so doing, treating the tumor in a subject in need. As described herein, such methods may employ the use of an effective amount of a first, a second, and/or a third composition. In certain embodiments, such compositions comprise an allogeneic leukemia-derived cell described herein, and may include pharmaceutical compositions and formulations, such as unit dose form compositions.

The pharmaceutical compositions and formulations generally include one or more optional pharmaceutically acceptable carriers and/or excipients. In certain embodiments, the compositions include at least one additional therapeutic agent (e.g., a second therapy having cytostatic or anticancer activity).

In certain embodiments, the present disclosure provides methods employing an immunogen that can be constituted in a composition, e.g., a pharmaceutical composition (e.g., an immunogenic pharmaceutical composition). In certain embodiments, the compositions comprise an allogeneic leukemia-derived cell and optionally a pharmaceutically acceptable carrier.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. Accordingly, there are a variety of suitable formulations. A pharmaceutically acceptable carrier includes, but is not limited to, a buffer, excipient, stabilizer, or preservative. In certain embodiments, the choice of carrier is determined in part by the particular cell and/or by the method of administration. A pharmaceutically acceptable carrier includes any and all solvents, dispersion media, coatings, antibacterial and antifungal agents, isotonic and absorption delaying agents, and the like that are physiologically compatible. In certain embodiments, the carrier for a composition containing, e.g., an allogeneic leukemia-derived cell, is suitable for intravenous, intramuscular, subcutaneous, parenteral, spinal or epidermal administration (e.g, by injection or infusion). In certain embodiments, where suitable, e.g., a small molecule based second therapy, the carrier for a composition containing the second therapy is suitable for non-parenteral, e.g, oral administration.

Formulations include those for oral, intravenous, intraperitoneal, subcutaneous, pulmonary, transdermal, intramuscular, intranasal, buccal, sublingual, or suppository administration. In certain embodiments, the cell populations are administered parenterally. The term "parenteral," as used herein, includes intravenous, intramuscular, subcutaneous, rectal, vaginal, and intraperitoneal administration. In certain embodiments, the cells are administered to the subject using peripheral systemic delivery by intravenous, intraperitoneal, or subcutaneous injection.

In certain embodiments, a method for generating an immune response against and/or treating a tumor in a subject in need, comprises one or more intratumoral administration steps each comprising administering to the subject at a tumor site, an effective amount of a first composition comprising an allogeneic leukemia-derived cell; and one or more vaccination steps each comprising administering to the subject at a site distal to the tumor site, an effective amount of a second composition comprising an allogeneic leukemia-derived cell. In certain embodiments, the first composition is prepared for intratumoral administration, and may comprise a diluent or solvent acceptable for intratumoral administration. In certain embodiments, the second composition is prepared for a route of administration selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue. In certain embodiments, the second composition is prepared for intravenous administration and may comprise a diluent or solvent acceptable for intravenous administration. In certain embodiments, the second composition is prepared for intradermal administration and may comprise a diluent or solvent acceptable for intradermal administration. In certain embodiments, the second composition is prepared for intramuscular administration and may comprise a diluent or solvent acceptable for intramuscular administration.

In certain embodiments, the intratumoral administration step(s) is(are) performed after the one or more vaccination steps. In such an embodiment, the method may further comprise one or more vaccination steps following the intratumoral administration step(s). The one or more vaccination steps following the intratumoral administration step(s) may each comprise administering an effective amount of a third composition comprising an allogeneic leukemia-derived cell via a route selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue. In certain embodiments, the third composition is prepared fora route of administration selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue. In certain embodiments, the third composition is prepared for intravenous administration and may comprise a diluent or solvent acceptable for intravenous administration. In certain embodiments, the third composition is prepared for intradermal administration and may comprise a diluent or solvent acceptable for intradermal administration. In certain embodiments, the third composition is prepared for intramuscular administration and may comprise a diluent or solvent acceptable for intramuscular administration.

A pharmaceutical composition of the disclosure can include one or more pharmaceutically acceptable salts, antioxidants, aqueous and non-aqueous carriers, and/or adjuvants such as preservatives, wetting agents, emulsifying agents and dispersing agents. Preparations acceptable for administration by a specific route of administration are known to those of skill in the art and may include the following.

Adjuvants known in the art, regardless of the route of administration, may be employed to improve/enhance the immunogenicity of a composition employed by the methods of the present disclosure. Adjuvants enhance the immunogenicity of a composition (e.g., a composition comprising an allogeneic leukemia-derived cell) but are not necessarily immunogenic themselves. Adjuvants have been used by those of skill in the art to improve immune responses to, e.g., vaccines. Adjuvants may be intrinsic or extrinsic. Intrinsic adjuvants may be derived from killed or attenuated bacteria used as vaccines. Extrinsic adjuvants may be an immune modulating substance non-covalently linked to antigens and are formulated to enhance immune responses.

In certain embodiments, the first, the second, and/or the third composition may comprise a T-cell immune response-eliciting adjuvant. The term "T-cell immune response-eliciting," as used in relation to adjuvants herein, refers to enhancing CD4+ and/or CD8+ T-cell immune responses or driving the immune response towards CD4+ and/or CD8+ T-cell activation. References that aid the skilled person in selecting adjuvants that direct the immune response towards cellular immunity are for instance Pashine et al., *Nature Medicine Supplement,* 11: S63-S68 (2005) and Awate et al., *Frontiers in Immunology,* 4:114, p. 1-10 (2013), the disclosures of which are incorporated by reference herein in their entirety. Examples of such adjuvants are aluminum mineral salts, oil-in-water emulsions, liposomes, toll-like receptor agonists or combinations thereof. Other adjuvants include liposomes, virosomes, MF59, Montanide, ISCOMs, QS-21, aluminum, ASO4, Poly I:C, MPL, GLA, imiquimod, CpG ODN, chitin, chitosan, β-glucan, or combinations thereof. (Temizoz et al. *Int Immunol.* 2016 July; 28(7): 329-338, the disclosure of which is incorporated by reference herein in its entirety).

In certain embodiments, adjuvants may be used specifically for parenteral modes of administration. Such adjuvants include, e.g., aluminum compounds (such as aluminum phosphate and aluminum hydroxide). The antigen can be precipitated with, or adsorbed onto, an aluminum compound according to standard protocols. Other adjuvants for parenteral modes of administration, as well as intratumoral or peritumoral modes of administration, are known to those of skill in the art.

In certain embodiments, the pharmaceutical composition can contain preservatives. Suitable preservatives may include, for example, methylparaben, propylparaben, sodium benzoate, and benzalkonium chloride. In certain embodiments, a mixture of two or more preservatives is used. The preservative or mixtures thereof are typically present in an amount of about 0.0001% to about 2% by weight of the total composition. Carriers are known to those of skill in the art, and are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in certain embodiments are included in the compositions. Suitable buffering agents include, for example, citric acid, sodium citrate, phosphoric acid, potassium phosphate, and various other acids and salts. In certain embodiments, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Compositions in certain embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations. The formulations to be used for in vivo administration are generally sterile. Sterility may be readily accomplished, e.g., by filtration through sterile filtration membranes.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present disclosure can be administered via one or more routes of administration using one or more of a variety of methods well known in the art.

As will be appreciated by the skilled artisan, the route and/or mode of administration will vary depending upon the desired results. Moreover, the skilled person is aware of other suitable compositions that are capable of mounting an immune response.

D. Methods of Treatment

Methods provided herein for eliciting an immune response against a tumor, and in so doing, treating the tumor in a subject in need, comprise one or more intratumoral administration steps and one or more vaccination steps. Such methods comprise one or more intratumoral administration steps each comprising administering an effective amount of a first composition at a tumor site, e.g., intratumorally or peritumorally, and one or more vaccination steps each comprising administering an effective amount of a second composition at a site distal to the tumor site.

In certain embodiments, the one or more intratumoral administration steps each comprises intratumorally or peritumorally administering an effective amount of the first composition. In certain embodiments, the intratumoral administration step comprises administering an effective amount of the first composition to the subject at the tumor site. In certain embodiments, the intratumoral administration step comprises administering an effective amount of the first composition into the tumor or proximal to the tumor. The intratumoral administration step, as used in a method described herein, is intended to encompass the administration of an effective amount of the first composition into a tumor (e.g., into an area that encompasses the tumor mass and surrounding tumor microenvironment). In certain embodiments, where the tumor may have less distinguishable boundaries and it is difficult for the skilled artisan (e.g., physician) to administer the first composition within the boundaries of a tumor, the intratumoral administration step is intended to encompass administration of the composition peritumorally (e.g., in the area immediately surrounding the tumor).

In certain embodiments, the one or more vaccination steps each comprise administering an effective amount of the second composition to a site distal to the tumor, i.e., a site that is away from the tumor. In certain embodiments, distal administration of the second composition in a vaccination step as described herein is through the parenteral route, which includes intravenous, intra-arterial, subcutaneous, intradermal, intranodal, intralymphatic and intramuscular administration, which are all well known to the person skilled in the art. In certain embodiments, distal administration of the second composition in a vaccination step as described herein is delivered by a mode selected from the group consisting of intramuscular injection, subcutaneous injection, intravenous injection, intraarterial injection, intraperitoneal injection, intrasternal injection, intradermal injection, transcutaneous injection, transdermal injection, and delivery to the interstitial space of a tissue. In certain embodiments, the one or more vaccination steps each comprise administering the second composition, wherein the administration is not intratumoral, but instead, is extratumoral and is, in some cases, intramuscular, intradermal, intravenous, intranodal, intralymphatic, or a combination thereof. In certain embodiments, the one or more vaccination steps each comprise administering the second composition intradermally at a site distal to the tumor site.

In certain embodiments, each of the one or more vaccination steps comprise administering the second composition via the same route of administration, e.g., each of the one or more vaccination steps comprise administering the second composition intradermally. In certain embodiments, one or more of the vaccination steps comprise administering the second composition via a different route of administration than at least one of the vaccination steps. For example, a method described herein comprising one or more vaccination steps may comprise a first vaccination step that is administered intradermally, and a second vaccination step that is administered intramuscularly. So long as the one or more vaccination steps are administered at a site distal to the tumor site, each of the one or more vaccination steps may be administered at different locations, or at the same location.

In certain embodiments, the one or more vaccination steps each comprise distally administering the second composition at a site at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1 mm, at least about 2 mm, at least about 3 mm, at least about 4 mm, at least about 5 mm, at least about 6 mm, at least about 7 mm, at least about 8 mm, at least about 9 mm, at least about 10 mm, at least about 15 mm, at least about 20 mm, at least about 25 mm, at least about 30 mm, at least about 35 mm, at least about 40 mm, at least about 45 mm, at least about 50 mm, at least about 60 mm, at least about 70 mm, at least about 80 mm, at least about 90 mm, at least about 10 cm, at least about 20 cm, at least about 30 cm, at least about 40 cm, at least about 50 cm, 50 cm or more away from the tumor (e.g., the edge of the tumor, or the center of the tumor). In certain embodiments, the one or more vaccination steps each comprise administering the second composition to the subject at a site distal to a tumor site, wherein the site distal to the tumor site is at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1 mm, at least about 2 mm, at least about 3 mm, at least about 4 mm, at least about 5 mm, at least about 6 mm, at least about 7 mm, at least about 8 mm, at least about 9 mm, at least about 10 mm, at least about 15 mm, at least about 20 mm, at least about 25 mm, at least about 30 mm, at least about 35 mm, at least about 40 mm, at least about 45 mm, at least about 50 mm, at least about 60 mm, at least about 70 mm, at least about 80 mm, at least about 90 mm, at least about 10 cm, at least about 20 cm, at least about 30 cm, at least about 40 cm, at least about 50 cm, 50 cm or more away from the tumor (e.g., the edge of the tumor, or the center of the tumor). Those of skill in the art will be able to discern a site that is distal to the tumor site.

In certain embodiments, the one or more vaccination steps each comprise distally administering the second composition at a site in an organ system that is different to the organ system in which the tumor resides. In certain embodiments, the one or more vaccination steps each comprise administering the second composition into an organ system that is different than the organ system in which the tumor resides. For example, if the tumor resides at or within an ovary (e.g., an epithelial ovarian cancer), the one or more vaccination steps each comprise distally administering the second composition at a site in an organ system that is not the ovary, e.g., the liver, kidney, etc. The term "organ" or "organ system" as used herein refers to a group of tissues with similar functions. Examples of organ systems include, without limitation, the muscular system, the digestive system (e.g., stomach, small intestine, large intestine, liver, pancreas, etc.), the respiratory system (e.g., lungs), the urinary system (e.g., kidneys, bladder, etc.), the reproductive organs (e.g., male and female reproductive system, ovaries, placenta, prostate, etc.), the endocrine system, the circulatory system, the nervous system (e.g., central and peripheral nervous systems), and the integumentary system (e.g., skin, subcutaneous tissue).

In certain embodiments, the one or more vaccination steps each comprise distally administering the second composition at a site contralateral to the tumor site. In certain embodiments, the one or more vaccination steps each comprise administering the second composition at a site contralateral to the tumor site. For example, if the tumor resides at or within an ovary, the one or more vaccination steps each comprise distally administering the second composition at or in the contralateral ovary. For example, if the tumor resides at or within the left ovary, the one or more vaccination steps each comprise distally administering the second composition to the right ovary. For example, if the tumor resides at or within an ovary, the one or more vaccination steps each comprise administering the second composition at or within the contralateral ovary. For example, if the tumor resides at or within the left ovary, the one or more vaccination steps each comprise administering the second composition to the right ovary.

In the case where the intratumoral administration step(s) is(are) performed after the one or more vaccination steps, a method as described herein may further comprise one or more vaccination steps following the intratumoral administration step(s). In certain embodiments, the one or more vaccination steps following the intratumoral administration step(s) each comprise administering an effective amount of a third composition comprising an allogeneic leukemia-derived cell via a route selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue. As will be appreciated by those of ordinary skill in the art, in certain embodiments, the third composition may be administered via the same route as the second composition. In certain embodiments, the third composition may be administered via a different route as the second composition.

Accordingly, provided herein is a method for generating an immune response against a tumor and/or treating a tumor in a subject in need thereof, comprising: (i) one or more intratumoral administration steps each comprising administering to the subject at a tumor site, an effective amount of a first composition; and (ii) one or more vaccination steps each comprising administering to the subject at a site distal to the tumor site, an effective amount of a second composition. In certain embodiments, the method comprises in the following order: (i) one or more intratumoral administration steps each comprising administering to the subject at a tumor site, an effective amount of a first composition; and (ii) one or more vaccination steps each comprising administering to the subject at a site distal to the tumor site, an effective amount of a second composition. In certain embodiments, the method comprises in the following order: (i) one or more vaccination steps each comprising administering to the subject at a site distal to a tumor site, an effective amount of a first composition; and (ii) one or more intratumoral administration steps each comprising administering to the subject at a tumor site, an effective amount of a second composition.

In methods that are carried out in the following order: (i) one or more vaccination steps each comprising administering to the subject at a site distal to a tumor site, an effective amount of a first composition; and (ii) one or more intratumoral administration steps each comprising administering to the subject at a tumor site, an effective amount of a second composition, the method may further comprise (iii) one or more vaccination steps following the one or more intratumoral administration steps, each comprising administering to the subject an effective amount of a third composition.

As described herein, a method of the present disclosure comprises one or more vaccination steps (e.g., one or more vaccination steps comprising administering a second composition, or one or more vaccination steps comprising administering a third composition). In certain embodiments, two, three, four, five, six, seven, or more vaccination steps are performed. The skilled artisan will recognize that any, if any, subsequent vaccination steps are performed, the subsequent vaccination steps are envisioned to incorporate any of the embodiments of a vaccination step described herein.

In certain embodiments, the one or more intratumoral administration steps and the one or more vaccination steps (e.g., the first of the one or more vaccination steps) are performed at substantially the same time. In certain embodiments, the one or more intratumoral administration steps and the first of the one or more vaccination steps are performed at substantially the same time. In certain embodiments, the one or more intratumoral administration step and the one or more vaccination steps (e.g., the first of the one or more vaccination steps) are performed on the same day.

In certain embodiments, the intratumoral administration step and the one or more vaccination steps (e.g., the first of the one or more vaccination steps) are temporally separated. Accordingly, in certain embodiments, the one or more intratumoral administration steps are performed before the one or more vaccination steps. In certain embodiments, the one or more intratumoral administration steps are performed after the one or more vaccination steps. In certain embodiments, a certain time has elapsed between the one or more intratumoral administration steps and the one or more vaccination steps. In certain embodiments, where the one or more intratumoral administration steps is/are performed first, the amount of time elapsed is sufficient for the subject to mount an immune response as a result of the one or more intratumoral administration steps. In certain embodiments, where the one or more intratumoral administration steps are performed second, the amount of time elapsed is sufficient for the subject to mount an immune response as a result of the one or more vaccination steps. It will be readily understood by the skilled artisan that the amount of time elapsed between the one or more intratumoral administration steps and the one or more vaccination steps is between the last of the one or more intratumoral administration steps, and the first of the one or more vaccination steps (where the one or more intratumoral administration steps are performed before the one or more vaccination steps). Where the one or more vaccination steps are performed before the one or more intratumoral administration steps, the skilled artisan understands that the time elapsed is between the last of the one or more vaccination steps and the first of the one or more intratumoral administration steps.

For example, a primary immune response can be mounted as a result of the one or more vaccination steps (e.g., the first of the one or more vaccination steps). In the case of a primary immune response, it may take from about 7 days to about 21 days to mount the primary immune response. In another example, a secondary immune response can be mounted as a result of the one or more vaccination steps (e.g., the first of the one or more vaccination steps). In the case of a secondary immune response, it may take from about 2 days to about 3 days to mount the secondary immune response. Accordingly, in certain embodiments, the time between the one or more intratumoral administration steps and the one or more vaccination steps is from about 1 day to about 21 days, from about 1 day to about 22 days, from about 1 day to about 23 days, from about 1 day to about 24 days, from about 1 day to about 3 weeks, from about 1 day to about 4 weeks, from about 1 day to about 5 weeks, from about 1 day to about 10 weeks, and any intervening amount of time thereof. In certain embodiments, the time between the one or more intratumoral administration steps and the one or more vaccination steps is about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 4 weeks, about 5 weeks, about 6 weeks, about 7 weeks, about 8 weeks, about 9 weeks, about 10 weeks, and any intervening amount of time thereof. In certain embodiments, the time between the one or more intratumoral administration steps and the one or more vaccination steps is about 2 days to about 21 days. In certain embodiments, the time between the one or more intratumoral administration steps and the one or more vaccination steps is about 2 days to about 3 days. In certain embodiments, the time between the one or more intratumoral administration steps and the one or more vaccination steps is about 7 days to about 21 days.

A subject that is suitable for receiving a method as described herein can be any subject that is capable of mounting a cellular immune response. For example, any mammal may be a suitable recipient of a method described herein. In certain embodiments, the subject is a human. In certain embodiments, the subject is a domesticated animal, e.g., a horse, a cow, a pig, a sheep, a dog, a cat, etc. In certain embodiments, the subject is an animal suitable for veterinary healthcare, e.g., a zoo animal.

In certain embodiments, the subject is a human suffering from a tumor (e.g., a solid tumor). In certain embodiments, the subject is a human who has previously suffered from a tumor, and/or has previously received treatment for a tumor. Such a subject could be suffering from relapse of the tumor. Accordingly, a suitable subject includes one that is suffering from relapse of a tumor. In certain embodiments, the subject is a domesticated animal suffering from a tumor (e.g., a solid tumor). In certain embodiments, the subject is an animal suitable for veterinary healthcare suffering from a tumor (e.g., a solid tumor). As used herein, an "animal suitable for veterinary healthcare" is any animal that is suitable for treatment by a veterinarian, and includes, without limitation, wild animals, domesticated animals, and zoo animals that are capable of mounting a cellular immune response. Tumors can be liquid or solid tumors. Examples of solid tumors include those that are classified as sarcomas, carcinomas, and lymphomas. In certain embodiments, the subject is suffering from a solid tumor. In certain embodiments, the subject is suffering from an ovarian cancer. In certain embodiments, the subject is suffering from a melanoma.

E. Combination Therapy

Methods provided herein are useful in generating an immune response against a tumor and/or treating the tumor. Such methods can be useful on their own, or in combination with other therapies (e.g., a second therapy). As such, also provided herein are combination therapies for use in combination with the methods described herein. For example, methods provided herein can be used in combination with radiation therapy, or with a second therapy having cytostatic or anticancer activity.

In certain embodiments, the methods described herein further comprise administering to a subject a second therapy. In some embodiments, the second therapy comprises an effective amount of a composition. In some embodiments, the second therapy comprises radiation therapy. In some embodiments, the second therapy comprises an immune checkpoint therapy. In some embodiments, the second therapy comprises an anti-angiogenesis therapy. In some embodiments, the second therapy comprises a poly(ADP-ribose) polymerase (PARP) inhibitor therapy. Those of skill in the art (e.g., physicians) would readily be able to determine the specific dosages and dosing regimens useful for a combination therapy described herein.

In certain aspects, methods provided herein are useful in combination with a second therapy having cytostatic or anticancer activity. Suitable cytostatic chemotherapy compounds include, but are not limited to DNA cross-linking agents, DNA-fragmenting agents, intercalating agents, protein synthesis inhibitors, topoisomerase I and II inhibitors, antimetabolites, microtubule-directed agents, kinase inhibitors, hormones and hormone antagonists.

In certain aspects, methods provided herein are useful in combination with a second therapy comprising one or more immunooncology (10) agents. 10 agents are known to be effective in enhancing, stimulating, and/or upregulating immune responses in a subject. In certain embodiments, use of an 10 agent in combination with a method described herein, can enhance the method's efficacy in treating a tumor. Examples of 10 agents include, without limitation, small molecule drugs, antibodies, and cell-based agents. In certain embodiments, an 10 agent is a monoclonal antibody, which can be a human antibody or humanized antibody. The 10 agent can be an agonist of a stimulatory receptor (e.g., a costimulatory receptor), or an antagonist of an inhibitory signal on T cell. The result of both include the amplification of antigen-specific T cell responses. Such 10 agents are also referred to in the art as immune checkpoint regulators (e.g., immune checkpoint inhibitors). In some embodiments, 10 agents regulate costimulatory and/or coinhibitory pathways, and are capable of augmenting and/or restoring the function of antigen-specific T cell responses. Examples of molecules involved in costimulatory and/or coinhibitory pathways include, without limitation, members of the immunoglobulin superfamily (IgSF); members of the B7 family of membrane proteins, including, for example, B7-1, B7-2, B7-H1 (PD-L1), B7-DC (PD-L2), B7-H2 (ICOS-L), B7-H3, B7-H4, B7-H5 (VISTA), and B7-H6; members of the tumor necrosis factor (TNF) superfamily, including, for example, CD40, CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fnl4, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, and NGFR.

Accordingly, in certain embodiments, the immune checkpoint therapy comprises the use of one or more immune checkpoint regulators that are (i) antagonists of a protein that inhibits T cell activation (e.g., immune checkpoint inhibitors), including, for example, CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; and (ii) agonists of a protein that stimulates T cell activation, including, for example, B7-1, B7-2, CD28, 4-1BB (CD137), 4-1BBL, ICOS, ICOS-L, OX40, OX40L, GITR, GITRL, CD70, CD27, CD40, DR3 and CD28H.

In certain embodiments, the second therapy as described herein may target one or more immune checkpoint regulators. Immune checkpoint regulators that may be targeted by a second therapy (e.g., an immune checkpoint inhibitor) of the present disclosure may include, without limitation, adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3), V-domain Ig suppressor of T cell activation (VISTA), and NKG2A.

In certain embodiments, the methods described herein further comprise administering to the subject an effective amount of an immune checkpoint inhibitor. In certain exemplary embodiments, the immune checkpoint inhibitor targets an immune checkpoint regulator selected from the group consisting of CTLA-4, PD-1, PD-L1, NKG2A, B7-H3, and B7-H4. In certain embodiments, immune checkpoint inhibitors may be small molecules, recombinant ligands, recombinant receptors, or antibodies. Immune checkpoint inhibitor antibodies may be humanized, human, chimerized, or any form of antibodies known in the art. Accordingly, in certain exemplary embodiments, the immune checkpoint inhibitor is an antibody selected from the group consisting of anti-CTLA-4, anti-PD-1, anti-PD-L1, anti-NKG2A, anti-B7-H3, and anti-B7-H4. In certain embodiments, the immune checkpoint inhibitor is an antibody selected from the group consisting of ipilimumab, pembrolizumab, nivolumab, atezolizumab, avelumab, durvalumab, and cemiplimab.

In certain embodiments, the immune checkpoint inhibitor is a PD-1 binding antagonist, a molecule that is capable of inhibiting the binding of PD-1 to its ligand binding partners. In certain embodiments, the PD-1 ligand binding partners are PD-L1 and/or PD-L2. In some embodiments, a PD-L1 binding antagonist is a molecule that inhibits the binding of PDL1 to its binding partners. In some embodiments, PD-L1 binding partners are PD-1 and/or B7-1. In some embodiments, the PD-L2 binding antagonist is a molecule that inhibits the binding of PD-L2 to its binding partners. In some embodiments, a binding partner of PD-L2 is PD-1. Exemplary antibodies are described in U.S. Pat. Nos. 8,735, 553, 8,354,509, and 8,008,449, the disclosure of which are incorporated herein by reference in their entireties.

In some embodiments, the immune checkpoint inhibitor is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. Nivolumab, also known as MDX-1106-04, MDX-1106, ONO-4538, BMS-936558, and OPDIVO, is an anti-PD-1 antibody described in International Patent Application No. WO2006/121168, the disclosure of which is incorporated herein in its entirety. Pembrolizumab, also known as MK-3475, Merck 3475, lambrolizumab, KEYTRUDA, and SCH-900475, is an anti-PD-1 antibody described in International Patent Application No. WO2009/114335, the disclosure of which is incorporated herein in its entirety. CT-011, also known as Pidilizumab, is an anti-PD-1 antibody described in International Patent Application No. WO2009/101611, the disclosure of which is incorporated herein in its entirety. Additional anti-PD-1 antibodies include PDR001 (Novartis; see WO2015/112900), MEDI-0680 (AMP-514) (AstraZeneca; see WO2012/145493), REGN-2810 (Sanofi/Regeneron; see WO2015/112800), JS001 (Taizhou Junshi), BGB-A317 (Beigene; see WO2015/35606), INCSHR1210 (SHR-1210) (Incyte/Jiangsu Hengrui Medicine; see WO2015/085847), TSR-042 (ANB001) (Tesara/AnaptysBio; see WO2014/179664), GLS-010 (Wuxi/Harbin Gloria Pharmaceuticals), AM-0001 (Armo/Ligand), or STI-1110 (Sorrento; see WO2014/194302).

In certain embodiments, the immune checkpoint inhibitor is a PD-L1 binding antagonist, such as an antagonistic PD-L1 antibody. Exemplary anti-PD-L1 antibody can be selected from Tecentriq (atezolizumab), durvalumab, avelumab, cemiplimab, STI-1014 (Sorrento; see WO2013/181634), or CX-072 (CytomX; see WO2016/149201). In some embodiments, the immune checkpoint inhibitor is a PD-L1 antagonist such as Durvalumab, also known as MED14736, atezolizumab, also known as MPDL3280A, or avelumab, also known as MSB00010118C.

In certain embodiments, the immune checkpoint inhibitor is a CTLA-4 binding antagonist, a molecule that is capable of inhibiting the binding of CTLA-4 to its ligand binding partners. CTLA-4 is found on the surface of T cells and acts as an "off" switch when bound to CD80 or CD86, also called B7-1 and B7-2 respectively, on the surface of antigen-presenting cells. CTLA4 is a member of the immunoglobulin superfamily that is expressed on the surface of Helper T cells and transmits an inhibitory signal to T cells. In some embodiments, the immune checkpoint inhibitor is an anti-CTLA-4 antibody (e.g., a human antibody, a humanized antibody, or a chimeric antibody). Anti-CTLA-4 antibodies are disclosed in U.S. Pat. No. 8,119,129, International Patent Application Nos. WO 01/14424, WO 98/42752; WO 00/37504 (CP675,206, also known as tremelimumab; formerly ticilimumab), U.S. Pat. No. 6,207,156; Hurwitz et al., 1998, the disclosures of which are incorporated herein by reference in their entireties. Antibodies that compete with any of these art-recognized antibodies for binding to CTLA-4 also can be used, for example, a humanized CTLA-4 antibody is described in International Patent Application Nos. WO2001014424, WO2000037504, and U.S. Pat. No. 8,017,114, the disclosures of which are incorporated herein by reference in their entireties. Exemplary anti-CTLA-4 antibodies include, ipilimumab (also known as 10D1, MDX-010, MDX-101, and Yervoy).

In certain embodiments, the immune checkpoint inhibitor is an antibody to B7-H4 (e.g., those disclosed in International Patent Application Nos. WO 2013025779 and WO2013067492, the disclosures of which are incorporated by reference herein in their entireties). In certain embodiments, the immune checkpoint inhibitor is an antibody to B7-H3, including without limitation antibodies neutralizing human B7-H3 (e.g. MGA271 disclosed as BRCA84D and derivatives in U.S. Patent Publication No. 20120294796, the disclosure of which is incorporated by reference herein in its entirety). In certain embodiments, the immune checkpoint inhibitor is an antibody to NKG2A, see, e.g., Montfoort et al. Cell (2018) 175(7):1744-1755, the disclosure of which is incorporated by reference herein in its entirety.

In certain aspects, methods provided herein are useful in combination with a second therapy comprising one or more anti-angiogenic agents. Accordingly, methods provided herein are useful in combination with anti-angiogenesis therapy. The formation of new blood vessels, or angiogenesis, facilitates cancer growth and metastasis by providing a tumor with dedicated blood supply to provide oxygen and essential nutrients required for its growth. Therapies targeting angiogenesis and associated growth factors including, without limitation, vascular endothelial growth factor (VEGF), platelet-derived growth factor (PDGF), and fibroblast growth factor (FGF), have been shown to inhibit new blood vessel growth.

Many anti-angiogenic agents are known in the art and would be suitable for use in combination with a method provided herein. Exemplary anti-angiogenic agents include, without limitation, physiological agents such as growth factors (e.g., ANG-2, NK1, 2, 4 (HGF), transforming growth factor beta (TGF-β)), cytokines (e.g., interferons such as IFN-α, -β, -γ, platelet factor 4 (PF-4), PR-39), proteases (e.g., cleaved AT-Ill, collagen XVIII fragment (Endostatin)), HmwKallikrein-d5 plasmin fragment (Angiostatin), prothrombin-F1-2, TSP-1), protease inhibitors (e.g., tissue inhibitor of metalloproteases such as TIMP-1, -2, or -3; maspin; plasminogen activator-inhibitors such as PAI-1; pigment epithelium derived factor (PEDF)), Tumstatin, antibody products (e.g., the collagen-binding antibodies HUIV26, HU177, XL313; anti-VEGF: anti-integrin (e.g., Vitaxin, (Lxsys))), and glycosidases (e.g., heparinase-I or -II). Also suitable are molecules that are antagonists to angiogenesis-associated antigens (including proteins and polypeptides), including, without limitation, molecules directed against VEGF, VEGF receptor, EGFR, bFGF, PDGF-B, PD-ECGF, TGFs including TGF-α, endoglin, Id proteins, various proteases, nitric oxide synthase, aminopeptidase, thrombospondins, k-ras, Wnt, cyclin-dependent kinases, microtubules, heat shock proteins, heparin-binding factors, synthases, collagen receptors, integrins, and surface proteoglycan NG2. "Chemical" or modified physiological agents known or believed to have anti-angiogenic potential include, for example, vinblastine, taxol, ketoconazole, thalidomide, dolestatin, combrestatin A, rapamycin (Cuba, et al. Nature Medicine (2002) 8:128-135, the disclosure of which is incorporated by reference herein in its entirety), CEP-7055 (available from Cephalon, Inc.), flavone acetic acid, Bay 12-9566 (Bayer Corp.), AG3340 (Agouron, Inc.). CGS. 27023A (Novartis), tetracylcine derivatives (e.g., COL-3 (Collagenix, Inc.)), Neovastat (Aeterna), BMS-275291 (Bristol-Myers Squibb), low dose 5-FU, low dose methotrexate (MTX), irsofladine, radicicol, cyclosporine, captopril, celecoxib, D45152-sulphated polysaccharide, cationic protein (Protarnine), cationic peptide-VEGF, Suramin (polysulphonated napthyl urea), compounds that interfere with the function or production of VEGF (e.g., SU5416 or SU6668 (Sugen), PTK787/ZK22584 (Novartis)), Distamycin A, Angiozyme (ribozyme), isoflavinoids, staurosporine derivatives, genistein, EMD121974 (Merck KcgaA), tyrphostins, isoquinolones, retinoic acid, carboxyamidotriazole, TNP-470, octreotide, 2-methoxyestradiol, aminosterols (e.g., squalamine), glutathione analogues (e.g., N-actyl-L-cysteine), combretastatin A-4 (Oxigene), Eph receptor blocking agents (Himanen et al. Nature (2001) 414(6866): 933-938, the disclosure of which is incorporated by reference herein in its entirety), Rh-Angiostatin, Rh-Endostatin (see, International Patent Application No. WO 01/93897, the disclosure of which is incorporated by reference herein in its entirety), cyclic-RGD peptide, accutin-disintegrin, benzodiazepenes, humanized anti-avb3 Ab, Rh-PAI-2, amiloride, p-amidobenzamidine, anti-uPA ab, anti-uPAR Ab, L-phenylalanine-N-methylamides (e.g., Batimistat, Marimastat), AG3340, and minocycline.

In certain embodiments, the anti-angiogenesis agent is an anti-VEGF antibody. Exemplary anti-VEGF antibodies include any antibodies, or antigen binding fragments thereof, that bind with sufficient affinity and specificity to VEGF and can reduce or inhibit the biological activity of VEGF. In certain embodiments, anti-VEGF antibodies include, without limitation, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. Cancer Research (1997) 57:4593-4599, the disclosure of which is incorporated by reference herein in its entirety. In certain embodiments, the anti-VEGF antibody is Bevacizumab (BV), also known as rhuMAb VEGF or AVASTIN. Bevacizumab and other humanized anti-VEGF antibodies are further described in U.S. Pat. No. 6,884,879, the disclosure of which is incorporated by reference herein in its entirety. Additional antibodies include, e.g., G6-31 and B20-4.1, as described in International Patent Application Nos. WO2005/012359 and WO2005/044853, the disclosures of which are incorporated by reference herein in their entireties. Additional anti-VEGF antibodies are described in the following U.S. Pat. Nos. 7,060,269, 6,582,959, 6,703,020, and 6,054,297; International Patent Publication Nos. WO98/45332, WO 96/30046, and WO94/10202; European Patent No. EP 0666868B1; U.S. Patent Publication Nos. 2006009360, 20050186208, 20030206899, 20030190317, 20030203409, and 20050112126; and Popkov et al., Journal of Immunological Methods 288:149-164 (2004), the disclosures of which are incorporated by reference herein in their entireties. Additional VEGF inhibitors include Sunitinib (Sutent®, Pfizer) and sorafenib (Nexavar®, Onyx and Bayer Healthcare Pharmaceuticals) which belong to a group of VEGF-receptor tyrosine-kinase inhibitors (RTKIs) with activity against both VEGFR and PDGFR. In certain embodiments, the anti-angiogenesis agent is sunitinib. Yet other VEGF inhibitors include fusion proteins that prevent ligand binding to vascular endothelial growth factor receptors (VEGFR). These fusion proteins are sometimes referred to as VEGF traps, and include aflibercept. Accordingly, in certain embodiments, the anti-angiogenesis therapy comprises an anti-angiogenesis agent selected from the group consisting of bevacizumab, aflibercept, sunitinib, and sorafenib.

In certain aspects, methods provided herein are useful in combination with a second therapy comprising one or more poly(ADP-ribose) polymerase (PARP) inhibitors. Accordingly, methods provided herein are useful in combination with PARP inhibitor therapy. PARP is a family of proteins involved in many functions in a cell, including DNA repair, gene expression, cell cycle control, intracellular trafficking and energy metabolism. PARP proteins play key roles in single strand break repair through the base excision repair pathway. PARP inhibitors have shown activity as a monotherapy against tumors with existing DNA repair defects, such as BRCA1 and BRCA2, and as a combination therapy when administered together with anti-cancer agents that induce DNA damage. The PARP inhibitor may be selected from the group consisting of a small molecule, a nucleic acid, a nucleic acid analog or derivative, a peptide, a peptidomimetic, a protein, an antibody or an antigen-binding fragment thereof, a monosaccharide, a disaccharide, a trisaccharide, an oligosaccharide, a polysaccharide, a lipid, a glycosaminoglycan, an extract made from a biological material, and combinations thereof. Exemplary PARP inhibitors include, without limitation, olaparib, veliparib or a prodrug thereof, rucaparib, talazoparib, niraparib, INO-1001, AZD2461, SC10914, BGB-290, and Fluzoparib. Accordingly, in certain embodiments, the PARP inhibitor therapy comprises a PARP inhibitor selected from the group consisting of olaparib, niraparib, rucaparib, and veliparib.

Combination therapies described herein comprising a method described herein (i.e., a first therapy) and a second therapy (e.g., immune checkpoint therapy, anti-angiogenesis therapy, PARP inhibitor therapy) encompass treatment regimens wherein the first therapy and the second therapy are simultaneously (e.g., substantially simultaneously) or sequentially administered to a subject. For example, a first therapy described herein can be substantially simultaneously administered to a subject together with the second therapy. Substantially simultaneous administration can be accomplished, for example, by administering to the subject a single dosage form having a fixed ratio of each therapy or in multiple, single dosage forms for each therapy. Each therapy can be sequentially or substantially simultaneously administered by any appropriate route including, without limitation, oral routes, intravenous routes, intratumoral routes, intramuscular routes, and direct absorption through mucous membrane tissues.

In some embodiments, the first therapy and the second therapy are administered by the same route or by different routes. For example, a first therapy of the combination selected may be administered by intravenous injection while the second therapy of the combination may be administered intratumorally. Alternatively, for example, all therapies may be administered intravenously or all therapeutic agents may be administered by intratumorally.

In some embodiments, a combination therapy can include the administration of the first therapy and the second therapy, in combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapies and non-drug treatment is achieved.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

F. Experimental Examples

Example 1: Efficacy of DCP-001 in a Humanized Ovarian Cancer Mouse Model: Vaccination Away from Tumor Site DCP-001 is an allogeneic off-the shelf whole cell based vaccine derived from the DCOne cell line. In brief, the cells were cultured in a cocktail of GM-CSF, TNFα, and IL-4 in the presence of mitoxantrone to accelerate differentiation of cells that have a dendritic cell phenotype, followed by maturation of the cells in the presence of prostaglandin-E2, TNFα, and IL-1β.

FIG. 1 depicts a schematic showing a vaccination strategy of an SKOV3 engrafted ovarian cancer mouse model. SKOV3 tumours were engrafted in humanized mice. DCP-001 was administered via intraperitoneal (IP) vaccination at a dose of 0.2E6 cells/mouse in prime boost fashion. Prime vaccination occurred at 36 days post-engraftment when tumor size was measured to be 75-100 mm$^3$. Boost vaccination occurred at 43 days post-engraftment. Controls were vaccinated with phosphate buffered saline (PBS) at days 36 and 43 post-engraftment. Tumor volume was measured three times a week until 63 days post-engraftment.

Figure 2:
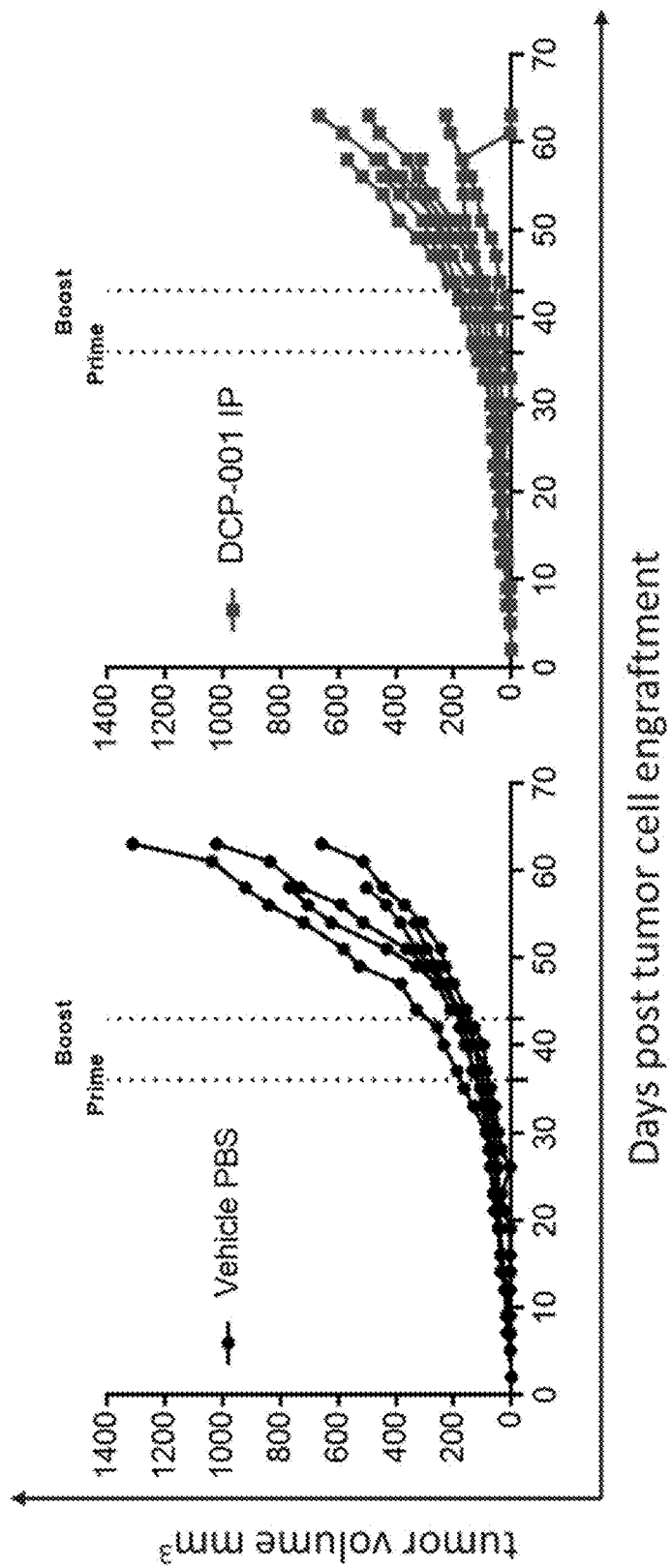
FIG. 2 depicts graphs showing the tumor volume (in $mm^3$) measured over time in SKOV3 tumor engrafted mice administered a vaccination strategy according to FIG. 1.

FIG. 2 depicts graphs showing the tumor volume (in mm$^3$) measured over time in SKOV3 tumor engrafted mice administered a vaccination according to the schedule depicted in FIG. 1. As shown in FIG. 2, tumor growth in DCP-001 vaccinated mice was found to be reduced compared to the control group (vaccinated with PBS). Tumor regression was observed in a mouse of the DCP-001 vaccinated group.

Figure 3:
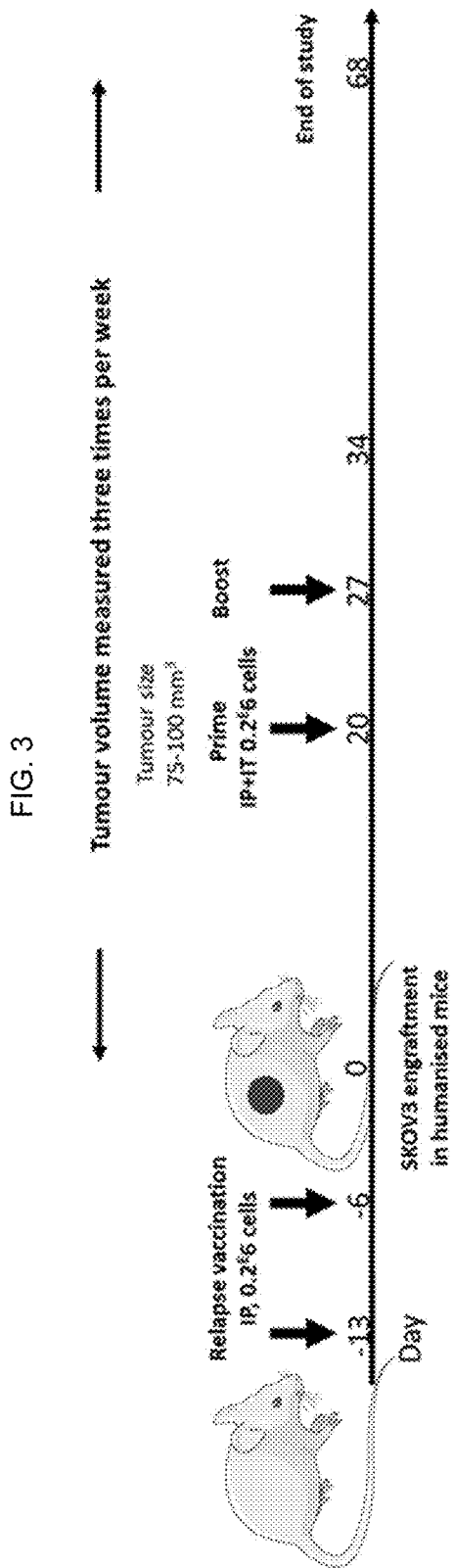
FIG. 3 depicts a schematic showing a vaccination strategy of an SKOV3 engrafted ovarian cancer mouse model, according to one embodiment.

Example 2: Efficacy of DCP-001 in a Humanized Ovarian Cancer Mouse Model: Different Vaccination Strategies FIG. 3 depicts a schematic showing a vaccination strategy of an SKOV3 engrafted ovarian cancer mouse model. SKOV3 tumours were engrafted in humanized mice. Two DCP-001 vaccination schedules were tested: (1) combination of intraperitoneal (IP) and intratumoral administration (IT) (n=9); and (2) relapse vaccination (n=9). Relapse vaccination aimed to prevent tumour recurrence following initial treatment. In the experimental setting, it was mimicked by vaccinating animals prior to tumor engraftment. In the combination vaccination schedule (DCP-001 IP+IT vaccination), 0.2E6 cells/mouse were administered on day 13 (prime) and day 20 (boost) post-tumour engraftment. In the relapse vaccination schedule, DCP-001 relapse vaccination of 0.2E6 cells/mouse were administered IP on days −13 and −6. Controls were vaccinated with PBS on days −13, −6, 13, and 43 (n=8).

FIG. 4 depicts a graph showing the tumor volume (in mm$^3$) measured over time in SKOV3 tumor engrafted mice administered control vaccination (PBS; FIG. 4A); combination vaccination (DCP-001 IP+IT; FIG. 4B); and relapse vaccination (FIG. 4C). As shown in FIG. 4A-FIG. 4C, tumor growth in both groups of DCP-001 vaccinated mice was reduced compared to the control group. In addition, tumor regression was observed in three mice of the IP+IT vaccinated group, and observed in five mice (three total and two partial regressions) of the relapse vaccinated group.

Figure 5:
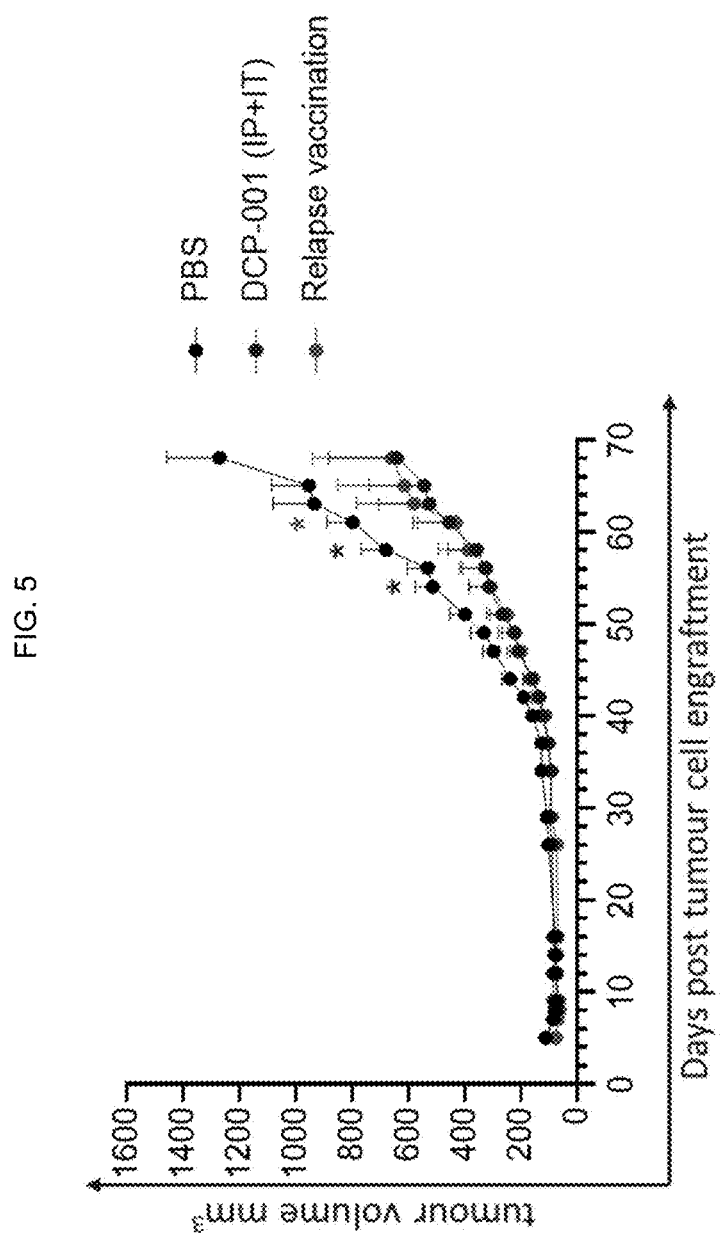
FIG. 5 depicts a graph showing the average tumor volume (in mm$^3$) measured over time in SKOV3 tumor engrafted mice administered control (PBS); combination vaccination (IP+IT); and relapse vaccination, as indicated.

FIG. 5 depicts a graph showing the average tumor volume (in mm$^3$) measured over time in SKOV3 tumor engrafted mice administered control (PBS); combination vaccination (IP+IT); and relapse vaccination, as indicated. In FIG. 5, * indicates p<0.05 using an unpaired t-test.

What is claimed is:

1. A method for treating a tumor in a subject in need thereof, comprising:
   one or more intratumoral administration steps each comprising administering to the subject at a tumor site, an effective amount of an allogeneic leukemia-derived cell, wherein the allogeneic leukemia-derived cell has a mature dendritic cell phenotype and is inactivated; and
   one or more vaccination steps each comprising administering to the subject at a site distal to the tumor site, an effective amount of the allogeneic leukemia-derived cell;
   wherein the allogeneic leukemia-derived cell comprises one or more exogenous tumor associated antigens or one or more nucleic acid molecules encoding the one or more exogenous tumor associated antigens.

2. The method of claim 1, wherein the one or more intratumoral administration steps each comprises administering the first composition into the tumor or at a site proximal to the tumor, optionally wherein the site proximal to the tumor is peritumoral.

3. The method of claim 1, wherein the first composition is prepared for intratumoral administration, optionally wherein the first composition comprises a diluent or solvent acceptable for intratumoral administration.

4. The method of claim 1, wherein the one or more vaccination steps each comprise administering the second composition via a route selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue.

5. The method of claim 1, wherein the one or more vaccination steps each comprises intravenously administering the second composition.

6. The method of claim 1, wherein the one or more intratumoral administration steps are performed before the one or more vaccination steps.

7. The method of claim 6,
   wherein
   the one or more vaccination steps following the one or more intratumoral administration steps each comprise administering to the subject an effective amount of a third composition comprising an allogeneic leukemia-derived cell via a route selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue.

8. The method of claim 1, wherein the time between the one or more intratumoral administration steps and the one or more vaccination steps is sufficient for an immune response to be mounted as a result of the one or more vaccination steps.

9. The method of claim 1, wherein the one or more intratumoral administration steps are performed at the same time as the one or more vaccination steps.

10. The method of claim 7, wherein the time between the one or more vaccination steps following the one or more intratumoral administration steps, and the one or more intratumoral administration steps is sufficient for an immune response to be mounted as a result of the first vaccination step of the one or more vaccination steps.

11. The method of claim 1,
    wherein the exogenous tumor associated antigen is selected from the group consisting of WT-1, MUC-1, RHAMM, PRAME, p53, and Survivin, or
    wherein the allogeneic leukemia-derived cell comprises WT-1, MUC-1, PRAME, and Survivin.

12. The method of claim 1, wherein the allogeneic leukemia-derived cell is derived from the DCOne cell line.

13. The method of claim 1, wherein the allogeneic leukemia-derived cell comprises a genetic aberration between chromosome 11p15.5 to 11p12, optionally wherein the genetic aberration encompasses about 16 Mb of genomic regions.

14. The method of claim 1, wherein the allogeneic leukemia-derived cell is CD34-positive, CD1a-positive, CD83-positive, CD80-positive, CD86-positive, and CD40-positive.

15. The method of claim 1, wherein the allogeneic leukemia-derived cell has been inactivated via irradiation.

16. The method of claim 7, wherein the first composition further comprises one or more pharmaceutically-acceptable carriers, adjuvants, excipients and/or diluents,
    the second composition further comprises one or more pharmaceutically-acceptable carriers, adjuvants, excipients and/or diluents, and/or
    the third composition further comprises one or more pharmaceutically-acceptable carriers, adjuvants, excipients and/or diluents.

17. The method of claim 1, wherein the subject has previously suffered from the tumor.

18. The method of claim 1, wherein the tumor is a solid tumor.

19. A method for treating a tumor in a subject in need thereof, comprising:
    one or more intratumoral administration steps each comprising administering to the subject an effective amount of an allogeneic leukemia-derived cell into the tumor or at a site proximal to the tumor, wherein the allogeneic leukemia-derived cell comprises a mature dendritic cell phenotype and is inactivated; and
    one or more vaccination steps each comprising administering to the subject at a site distal to the tumor site, an effective amount of the allogeneic leukemia-derived cell via a route selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue;
    wherein the allogeneic leukemia-derived cell comprises one or more exogenous tumor associated antigens or one or more nucleic acid molecules encoding the one or more exogenous tumor associated antigens.

20. The method of claim 6, wherein the one or more vaccination steps following the one or more intratumoral administration steps are administered via the same route as the one or more vaccination steps.

21. The method of claim 6, wherein the one or more vaccination steps following the one or more intratumoral administration steps are administered via a different route as the one or more vaccination steps.

22. The method of claim 1, wherein the time between the one or more intratumoral administration steps and the one or more vaccination steps is sufficient for an immune response to be mounted as a result of the first vaccination step of the one or more vaccination steps.

23. The method of claim 1, wherein-the time between the one or more intratumoral administration steps and the one or more vaccination steps is about 2 days to about 21 days.

24. The method of claim 1, wherein the one or more intratumoral administration steps are performed at the same time as the first vaccination step of the one or more vaccination steps.

25. The method of claim 7, wherein the time between the one or more vaccination steps following the one or more intratumoral administration steps, and the one or more intratumoral administration steps is about 2 days to about 21 days.

26. The method of claim 7, wherein the one or more vaccination steps following the one or more intratumoral administration steps, and the one or more intratumoral administration steps are performed at the same time.

\* \* \* \* \*